(12) United States Patent
Kuriyama

(10) Patent No.: US 10,820,787 B2
(45) Date of Patent: Nov. 3, 2020

(54) ENDOSCOPE DEVICE AND FOCUS CONTROL METHOD FOR ENDOSCOPE DEVICE

(71) Applicant: OLYMPUS CORPORATION, Hachioji (JP)

(72) Inventor: Naoya Kuriyama, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 606 days.

(21) Appl. No.: 15/656,638

(22) Filed: Jul. 21, 2017

(65) Prior Publication Data

US 2017/0319051 A1 Nov. 9, 2017

Related U.S. Application Data

(63) Continuation of application No. PCT/JP2015/051785, filed on Jan. 23, 2015.

(51) Int. Cl.
*A61B 1/04* (2006.01)
*A61B 1/00* (2006.01)
(Continued)

(52) U.S. Cl.
CPC ...... *A61B 1/00188* (2013.01); *A61B 1/00006* (2013.01); *A61B 1/00009* (2013.01);
(Continued)

(58) Field of Classification Search
CPC ............ A61B 1/00188; A61B 1/00006; A61B 1/00009; G03B 13/36
See application file for complete search history.

(56) References Cited

U.S. PATENT DOCUMENTS 9,645,473 B2 * 5/2017 Tsuruoka .......... G02B 23/2484
2008/0084483 A1 * 4/2008 Kusaka .............. H04N 5/23212
348/222.1
(Continued)

FOREIGN PATENT DOCUMENTS

JP 2006334297 A 12/2006
JP 2009239515 A 10/2009
(Continued)

OTHER PUBLICATIONS

International Search Report (ISR) and Written Opinion dated Apr. 21, 2015 issued in International Application No. PCT/JP2015/051785.

*Primary Examiner* — Matthew J Kasztejna
(74) *Attorney, Agent, or Firm* — Holtz, Holtz & Volek PC

(57) ABSTRACT

An endoscope apparatus comprises a processor comprising hardware. The processor is configured to implement a motion amount calculation process and a focus control process. The processor implements the motion amount calculation process that calculates a plurality of local motion amounts, calculates a correlation between each of the plurality of local motion amounts and a peripheral local motion amount, and calculates the relative motion amount based on a local motion amount among the plurality of local motion amounts that has the correlation higher than a given correlation. And the processor implements the focus control process that calculates a cumulative motion amount by accumulating the relative motion amount over N frames (wherein N is a natural number equal to or larger than 3), and causes the imaging section to perform a focus operation when it has been determined that the cumulative motion amount is larger than the first threshold value.

21 Claims, 15 Drawing Sheets

(51) Int. Cl.
  *A61B 1/045* (2006.01)
  *A61B 1/06* (2006.01)
  *G02B 23/24* (2006.01)

(52) U.S. Cl.
  CPC .............. *A61B 1/042* (2013.01); *A61B 1/045* (2013.01); *A61B 1/0638* (2013.01); *A61B 1/0669* (2013.01); *G02B 23/243* (2013.01)

(56) References Cited

U.S. PATENT DOCUMENTS

| | | |
|---|---|---|
| 2010/0194869 A1 | 8/2010 | Matsuzaki |
| 2010/0265342 A1 | 10/2010 | Liang et al. |
| 2011/0279727 A1* | 11/2011 | Kusaka ............. H01L 27/14621 348/340 |
| 2012/0026386 A1* | 2/2012 | Tomita .................... G02B 7/36 348/345 |
| 2013/0165753 A1 | 6/2013 | Takahashi |
| 2014/0146182 A1 | 5/2014 | Endo |
| 2014/0300716 A1 | 10/2014 | Tsuruoka |
| 2015/0296125 A1* | 10/2015 | Kusaka .................... G02B 7/34 348/349 |
| 2018/0310812 A1* | 11/2018 | Kuriyama .......... A61B 1/00188 |

FOREIGN PATENT DOCUMENTS

| | | |
|---|---|---|
| JP | 2010176569 A | 8/2010 |
| JP | 2010190913 A | 9/2010 |
| JP | 2010191080 A | 9/2010 |
| JP | 2012055498 A | 3/2012 |
| JP | 2012524500 A | 10/2012 |
| JP | 2013043007 A | 3/2013 |
| JP | 2013146289 A | 8/2013 |
| WO | 2013021767 A1 | 2/2013 |

* cited by examiner

| G | R | G | R | G | R | G | R |
|---|---|---|---|---|---|---|---|
| B | G | B | G | B | G | B | G |
| G | R | G | R | G | R | G | R |
| B | G | B | G | B | G | B | G |
| G | R | G | R | G | R | G | R |
| B | G | B | G | B | G | B | G |
| G | R | G | R | G | R | G | R |
| B | G | B | G | B | G | B | G |

FIG. 9

| | | MAGNITUDE (NUMBER OF PIXELS) | | | | | | | | | | |
|---|---|---|---|---|---|---|---|---|---|---|---|---|
| | | 0 | 1~7 | 8~15 | 16~23 | 24~31 | 32~39 | 40~47 | 48~55 | 56~63 | 64~71 | 72~80 |
| DIRECTION | · | 0 | | | | | | | | | | |
| | ↑ | | 0 | 0 | 0 | 0 | 0 | 0 | 0 | 0 | 0 | 0 |
| | ↗ | | 0 | 0 | 2 | 0 | 0 | 0 | 0 | 0 | 0 | 0 |
| | → | | 0 | 11 | 0 | 0 | 0 | 0 | 0 | 0 | 0 | 0 |
| | ↘ | | 0 | 0 | 0 | 0 | 0 | 0 | 0 | 0 | 0 | 0 |
| | ↓ | | 0 | 0 | 0 | 0 | 0 | 0 | 0 | 0 | 0 | 0 |
| | ↙ | | 0 | 2 | 0 | 0 | 0 | 0 | 0 | 0 | 0 | 0 |
| | ← | | 0 | 0 | 0 | 0 | 0 | 0 | 0 | 0 | 0 | 0 |
| | ↖ | | 0 | 0 | 0 | 0 | 0 | 0 | 0 | 0 | 0 | 0 |

ENDOSCOPE DEVICE AND FOCUS CONTROL METHOD FOR ENDOSCOPE DEVICE

CROSS REFERENCE TO RELATED APPLICATION

This application is a continuation of International Patent Application No. PCT/JP2015/051785, having an international filing date of Jan. 23, 2015, which designated the United States, the entirety of which is incorporated herein by reference.

BACKGROUND

A depth of field as deep as possible is required for an endoscope apparatus (endoscope system) so that the user can easily perform diagnosis and treatment. In recent years, the depth of field of an endoscope apparatus has become shallow along with the use of an image sensor having a large number of pixels, and an endoscope apparatus that performs an autofocus (AF) process has been proposed.

Examples of a known AF control process include the following methods. A first method is used to implement an AF process that is used for a video camera or the like, and performs a focus operation using a change in contrast within an image as a trigger. A second method is disclosed in JP-A-2010-191080. The second method detects a relative change in position with respect to the object and a camera using a motion sensor, and performs a focus operation when the output (e.g., angular acceleration or acceleration) from the motion sensor has become equal to or larger than a given amount.

SUMMARY

According to one aspect of the invention, there is provided an endoscope apparatus comprising:
a processor comprising hardware,
the processor being configured to implement:
a motion amount calculation process that calculates a relative motion amount that is a relative motion amount with respect to an imaging section and an object; and
a focus control process that is performed on the imaging section,
wherein the relative motion amount comprises information about a magnitude of a motion and information about a direction of a motion,
the processor implements the motion amount calculation process that calculates a plurality of local motion amounts, calculates a correlation between each of the plurality of local motion amounts and a peripheral local motion amount, and calculates the relative motion amount based on a local motion amount among the plurality of local motion amounts that has the correlation higher than a given correlation, and
the processor implements the focus control process that calculates a cumulative motion amount by accumulating the relative motion amount over N frames (wherein N is a natural number equal to or larger than 3), performs a focus necessity determination process that determines whether or not the cumulative motion amount is larger than a first threshold value, and causes the imaging section to perform a focus operation when it has been determined that the cumulative motion amount is larger than the first threshold value.

According to another aspect of the invention, there is provided a focus control method for an endoscope apparatus comprising:
calculating a plurality of local motion amounts;
calculating a correlation between each of the plurality of local motion amounts and a peripheral local motion amount;
calculating a relative motion amount based on a local motion amount among the plurality of local motion amounts that has the correlation higher than a given correlation, the relative motion amount being a relative motion amount with respect to an imaging section and an object;
calculating a cumulative motion amount by accumulating the relative motion amount over N frames (wherein N is a natural number equal to or larger than 3), the relative motion amount comprising information about a magnitude of a motion and information about a direction of a motion;
performing a focus necessity determination process that determines whether or not the cumulative motion amount is larger than a first threshold value; and
causing the imaging section to perform a focus operation when it has been determined that the cumulative motion amount is larger than the first threshold value.

BRIEF DESCRIPTION OF THE DRAWINGS

FIG. 9 illustrates an example of a two-dimensional histogram.

DESCRIPTION OF EXEMPLARY EMBODIMENTS

The exemplary embodiments of the invention are described below. Note that the exemplary embodiments described below do not in any way limit the scope of the invention laid out in the claims. Note also that all of the elements described below in connection with the exemplary embodiments should not necessarily be taken as essential elements of the invention.

1. First Embodiment

For example, the first method that uses a change in contrast as a trigger, and the second method that uses a situation in which the output from the motion sensor has become equal to or larger than a given amount, as a trigger (see above), are known as the AF control method. A case where the first method or the second method is applied to an endoscopic procedure is discussed below.

Figure 1:
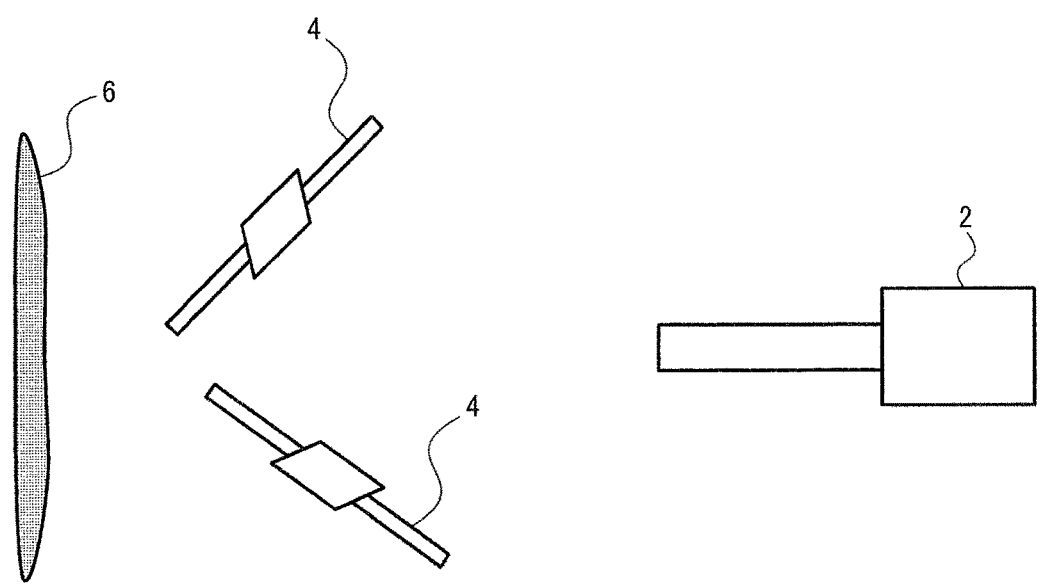
FIG. 1 is a view illustrating an endoscopic procedure.

As illustrated in FIG. 1, when an endoscopic procedure is performed using an endoscope apparatus 2, a treatment (e.g., excision of a lesion, or suture) is performed on an object 6 (tissue) using a treatment tool 4 (e.g., electrosurgical knife or forceps). When the first method is applied to the endoscopic procedure, since the treatment tool 4 is included in the captured image in addition to the object 6, and makes a motion based on the operation performed by the user, a change in contrast occurs even when the imaging range or the focus state has not changed. An unnecessary focus operation may be performed due to a change in contrast caused by the treatment tool 4, and it is difficult to implement a stable AF control process when the treatment tool 4 is operated.

When the second method is applied to the endoscopic procedure, since the focus operation is not performed when the output from the motion sensor is less than a given amount, the focus operation may not be performed even when the object is out of focus. For example, when a motion whereby the output from the motion sensor is less than a given amount has continuously occurred in an identical direction, the focus operation is not performed although the imaging range has moved to a large extent (or the object lies outside the depth of field). When a motion whereby the output from the motion sensor momentarily becomes equal to or larger than a given amount has occurred due to shake or the like, the focus operation is performed although the imaging range substantially has not changed (or the object lies within the depth of field). The usability of the endoscope apparatus may be impaired if the focus operation is unintentionally performed.

As described above, the known AF control methods have a problem in that an unnecessary focus operation is performed, or a necessary focus operation is not performed, during various scenes that may occur when an endoscopic procedure is performed.

Figure 2:
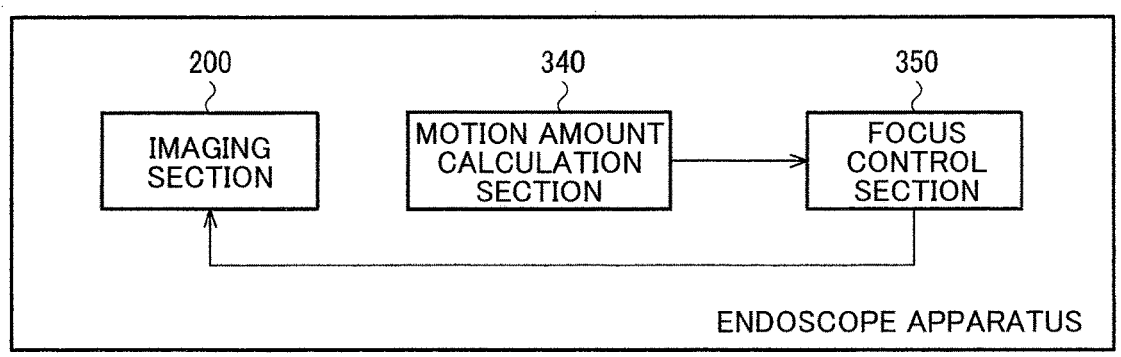
FIG. 2 illustrates a configuration example of an endoscope apparatus (first embodiment).

FIG. 2 illustrates a configuration example of an endoscope apparatus according to a first embodiment that can solve the above problem. The endoscope apparatus includes an imaging section 200, a motion amount calculation section 340 that calculates a relative motion amount that is a relative motion amount with respect to the imaging section 200 and an object, and a focus control section 350 (AF control section) that performs a focus control process on the imaging section 200. Note that the imaging section 200 may be configured to be removable from the endoscope apparatus, and the endoscope apparatus may not include the imaging section 200.

The focus control section 350 calculates a cumulative motion amount by accumulating the relative motion amount over N frames (wherein N is a natural number equal to or larger than 3), perform a focus necessity determination process that determines whether or not the cumulative motion amount is larger than a first threshold value, and causes the imaging section 200 to perform a focus operation when it has been determined that the cumulative motion amount is larger than the first threshold value.

An appropriate focus control process that is required during various scenes that may occur when an endoscopic procedure is performed, can be implemented by utilizing the cumulative motion amount. The object that is captured using an endoscope apparatus may be tissue and a treatment tool, for example. The focus operation is required when the imaging range with respect to the tissue has changed (moved), or when the tissue or the treatment tool lies outside the depth of field, for example. If the focus operation is performed when such a situation has not occurred, a decrease in visibility may occur due to a temporary change in focus state. For example, the treatment tool is operated during a procedure without changing (moving) the imaging range. In this case, the procedure is hindered if a change in focus state has occurred during the procedure. According to the first embodiment, it is possible to perform the focus operation when the focus operation is required (e.g., when the imaging range with respect to the tissue has changed (moved), or when the tissue or the treatment tool lies outside the depth of field). On the other hand, the focus operation is not performed when the focus operation is not required (e.g., when only the treatment tool makes a motion).

More specifically, even when the contrast of the image changes due to the manipulation of the treatment tool, a focus control process that is not affected by the manipulation of the treatment tool can be implemented by utilizing the motion amount as a trigger. Even when a small movement in an identical direction has occurred continuously, it is possible to detect a large motion amount (i.e., detect a change (movement) in imaging range, or detect an out-of-focus state), and implement the focus operation, by accumulating the motion amount. Since the cumulative motion amount is small (i.e., it is determined that a change (movement) in imaging range or an out-of-focus state has not occurred) even when a large momentary motion has occurred provided that a motion other than such a momentary motion is small, it is possible to suppress or reduce a situation in which the focus operation is unintentionally performed. Moreover, it is considered that random motions are averaged by accumulating the motion amount. For example, it is considered that a treatment tool makes a random motion rather than continuously making a motion in a constant direction. Therefore, the motion amount of the treatment tool decreases through accumulation, and the cumulative motion amount of the tissue increases when a motion in a constant direction (i.e., a relative motion with respect to the imaging section and the tissue in a constant direction) has occurred with respect to the imaging range of the tissue.

When detecting a large movement (e.g., movement of the imaging range, or movement by which the object lies outside the depth of field), it is difficult to perform a matching process from the image that corresponds to the frame before the movement occurs, and the image that corresponds to the frame after the movement has occurred (i.e., images captured at an N frame interval). According to the first embodiment, the relative moving amount is detected at a small interval (e.g., the relative moving amount is detected between frames), and accumulated to detect a large movement.

The term "motion amount" used herein refers to an amount that changes corresponding to a relative change in position (e.g., a movement that does not change the optical axis direction of the camera) or a relative change in direction (e.g., a rotation (pan or tilt) that changes the optical axis direction of the camera) with respect to the imaging section 200 and the object. For example, when a motion vector is detected from an image, the magnitude or the direction of the motion vector changes corresponding to the movement or the rotation of the imaging section 200. When a motion sensor is used, an acceleration, an angular acceleration, an angular velocity, and the like that correspond to the movement or the rotation of the imaging section 200 are obtained. The motion amount is an amount that represents the information about the magnitude of the motion and the information about the direction of the motion. The motion amount may be an amount that represents one of the information about the magnitude of the motion and the information about the direction of the motion For example, "+1" is assigned to a horizontal-to-optical axis motion that moves closer to the object, "−1" is assigned to a horizontal-to-optical axis motion that moves away from the object, and "0" is assigned when no horizontal-to-optical axis motion has occurred (as described later). Specifically, the horizontal-to-optical axis motion amount is an amount that represents the direction of the motion along the optical axis direction. In the first embodiment, it is desirable that the motion amount include at least the information about the direction of the motion. When the motion amount includes the information about the direction of the motion, the motion in a given direction is accumulated to detect the relative movement (i.e., movement of the imaging range, or movement by which the object lies outside the depth of field) with respect to the imaging section 200 and the object.

The first threshold value is a threshold value that is used to detect the relative movement with respect to the imaging section 200 and the object that is represented by the cumulative motion amount. Specifically, the relative motion amount is a motion amount that corresponds to an interval shorter than N frames (e.g., inter-frame motion amount), and the cumulative motion amount is obtained by accumulating (e.g., adding up or integrating) the relative motion amount. Therefore, the cumulative motion amount represents a motion that corresponds to an interval longer than that of the relative motion amount (i.e., the moving amount over N frames). For example, the relative motion amount corresponds to the speed of the motion, and the moving amount (distance or direction) obtained by integrating the relative motion amount corresponds to the cumulative motion amount. The moving amount can be determined by performing a threshold value determination process on the cumulative motion amount. For example, a value that corresponds to ⅓rd or ½nd of the image size may be used as the first threshold value. In this case, the focus operation is performed when the object has moved within the image by ⅓rd or ½nd of the image size (i.e., when the imaging range has moved). Alternatively, a value that corresponds to the depth of field may be used as the first threshold value. In this case, the focus operation is performed when the object lies outside the depth of field. Note that the cumulative motion amount need not necessarily be an amount that accurately represents the magnitude of the movement, but may be an amount that roughly represents the magnitude of the movement. For example, the cumulative motion amount may be an amount obtained by accumulating the information about the direction of the motion (e.g., the motion amount when "+1" is assigned to a motion that moves closer to the object, "−1" is assigned to a motion that moves away from the object, and "0" is assigned when no motion has occurred).

The N frames refer to the number of frames over which the relative motion amount is accumulated. N is not limited to a fixed number, but may be a variable number. For example, the relative motion amount may be accumulated from a reference frame (see the second embodiment). In this case, "N=3" in the third frame from the reference frame, and "N=10" in the tenth frame from the reference frame. Alternatively, N may be set to a given number, and the relative motion amount may be accumulated from the current frame up to the Nth previous frame. In this case, N is set to the given number even when the current frame has changed.

The term "focus control process" includes a focus operation that adjusts the focus, a standby state in which the focus is not adjusted, and a transition control process, and the like. The term "focus control process" refers to a process that controls the focus of the imaging section. The term "focus operation" refers to a series of operations that bring the object into focus. For example, the focus operation may be implemented using a contrast method (hill-climbing method), a method that determines the in-focus direction by means of wobbling, or the like.

The endoscope apparatus according to the embodiments of the invention may be configured as described below. Specifically, the endoscope apparatus according to the embodiments of the invention may include a memory that stores information (e.g., a program and various types of data), and a processor (i.e., a processor including hardware) that operates based on the information stored in the memory. The processor performs a motion amount calculation process that calculates a relative motion amount that is a relative motion amount with respect to the imaging section 200 and the object, and a focus control process that is performed on the imaging section 200. The processor performs the focus control process that calculates a cumulative motion amount by accumulating the relative motion amount over N frames, performs a focus necessity determination process that determines whether or not the cumulative motion amount is larger than a first threshold value, and causes the imaging section 200 to perform a focus operation when it has been determined that the cumulative motion amount is larger than the first threshold value.

The processor may implement the function of each section by individual hardware, or may implement the function of each section by integrated hardware, for example. The processor may comprise hardware, and the hardware may include at least one of a circuit that processes digital signal, and a circuit that processes analog signal, for example. The processor may a circuit device (e.g. an integrated circuit, and the like) or a plurality of circuit devices that is/are implemented on a circuit board, or a circuit element (e.g. a register, capacitor, and the like) or a plurality of circuit elements that is/are implemented on a circuit board, for example. The processor may implement the function of each section by individual hardware, or may implement the function of each section by integrated hardware, for example. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The processor may include an amplifier, a filter, or the like that processes analog signal. The memory may be a semiconductor memory (e.g., SRAM or DRAM), a register, a magnetic storage device (e.g., hard disk drive), or an optical storage device (e.g., optical disk device). For example, the memory stores a computer-readable instruction. Each section of the endoscope apparatus (i.e., the processing section (e.g., the processing section 300 illustrated in FIG. 3) included in the endoscope apparatus) is implemented by causing the processor to execute the instruction. The instruction may be an instruction included in an instruction set that is included in a program, or may be an instruction that causes a hardware circuit included in the processor to operate.

The operation according to the embodiments of the invention is implemented as described below, for example. The processor calculates a relative motion amount that is a relative motion amount with respect to the imaging section 200 and the object, and stores the relative motion amount in the memory. The processor calculates a cumulative motion amount by accumulating the relative motion amount stored in the memory over N frames, and stores the cumulative motion amount in the memory. The processor reads the cumulative motion amount from the memory, performs a focus necessity determination process that determines whether or not the cumulative motion amount is larger than a first threshold value, and causes the imaging section 200 to perform a focus operation when it has been determined that the cumulative motion amount is larger than the first threshold value.

Each section of the endoscope apparatus according to the embodiments of the invention (i.e., the processing section (e.g., the processing section 300 illustrated in FIG. 3) included in the endoscope apparatus) may be implemented as a module of a program that operates on the processor. For example, the motion amount calculation section 340 is implemented as a motion amount calculation module that calculates a relative motion amount that is a relative motion amount with respect to the imaging section 200 and the object. The focus control section 350 is implemented as a focus control module that calculates a cumulative motion amount by accumulating the relative motion amount over N frames, performs a focus necessity determination process that determines whether or not the cumulative motion amount is larger than a first threshold value, and causes the imaging section 200 to perform a focus operation when it has been determined that the cumulative motion amount is larger than the first threshold value.

2. Second Embodiment

2.1. Endoscope Apparatus

Figure 3:
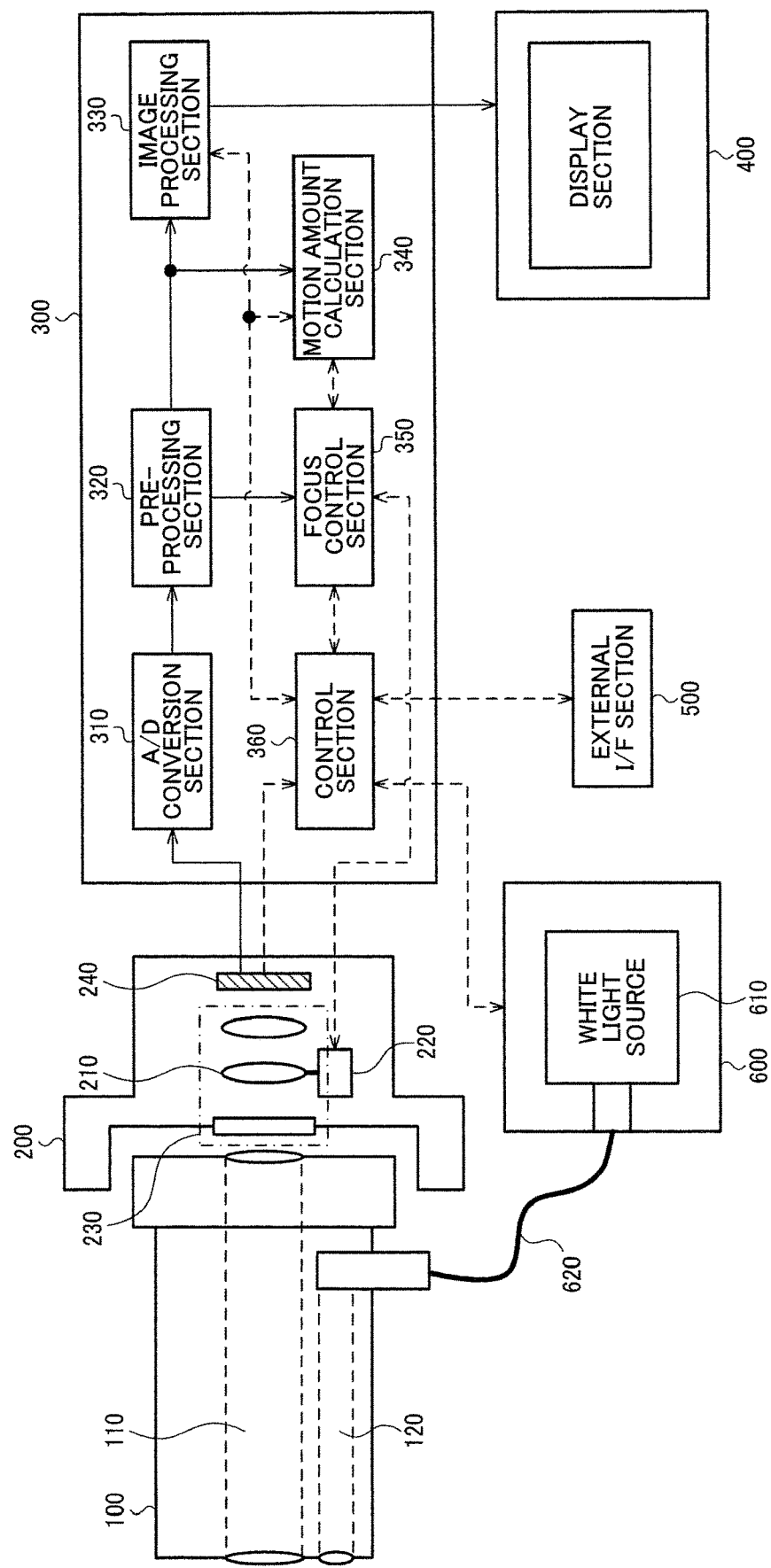
FIG. 3 illustrates a configuration example of an endoscope apparatus (second embodiment).

FIG. 3 illustrates a configuration example of an endoscope apparatus (endoscope system) according to a second embodiment. The endoscope apparatus includes a rigid scope 100 that is inserted into a body, an imaging section 200 that is connected to the rigid scope 100, a processing section 300, a display section 400, an external OF section 500, and a light source section 600.

The endoscope apparatus that utilizes the rigid scope 100 is used for surgery such as laparoscopic surgery. More specifically, a small hole is formed in the abdominal region of a living body, for example. The rigid scope 100 is inserted into the small hole, and a treatment tool is inserted into the same small hole or another small hole. A surgical procedure is performed using the treatment tool within the field of view of the rigid scope 100. Examples of the treatment tool include a surgical knife, forceps, a needle/suture, a washing water supply/suction tool, and the like. Note that the focus control method according to the second embodiment can also be applied to an endoscope apparatus that utilizes a flexible scope instead of an endoscope apparatus that utilizes the rigid scope 100.

The light source section 600 includes a white light source 610 that emits white light, and a light guide cable 620 that guides the light emitted from the white light source 610 to the rigid scope 100. The rigid scope 100 includes a lens system 110 that includes an imaging lens, a relay lens, an eyepiece, and the like, and a light guide section 120 that guides the light emitted from the light guide cable 620 to the end of the rigid scope 100. The imaging section 200 includes an objective lens system 230 that forms an image from the light that has passed through the lens system 110 (i.e., the reflected light from the object). The objective lens system 230 includes a focus lens 210 that adjusts the in-focus object plane position. The imaging section 200 also includes an image sensor 240 that photoelectrically converts the reflected light that has passed through the objective lens system 230 to generate an image, and a focus lens driver section 220 that drives the focus lens 210. The focus lens driver section 220 is implemented by a voice coil motor (VCM), for example.

Note that the term "in-focus object plane position" used herein refers to the position of the object at which the imaging section 200 brings the object into focus. More specifically, the in-focus object plane (or the object-side focal point) is determined with respect to the objective lens system 230 corresponding to the image plane (or the image-side focal point). The term "in-focus object plane position" used herein refers to the in-focus object plane when the image plane coincides with the image plane of the image sensor 240. The in-focus object plane position is a relative position with respect to the imaging section 200 and the in-focus object plane. For example, the in-focus object plane position is represented by the distance from a reference point (e.g., the end of the objective lens system 230, or the end of the rigid scope 100) of the imaging section 200 to the in-focus object plane (i.e., the in-focus object-side plane with respect to the optical system). The in-focus object plane position can be determined from the control information (position) about the focus lens 210, and the optical properties (design values) of the objective lens system 230, for example.

Figures 4, 5:
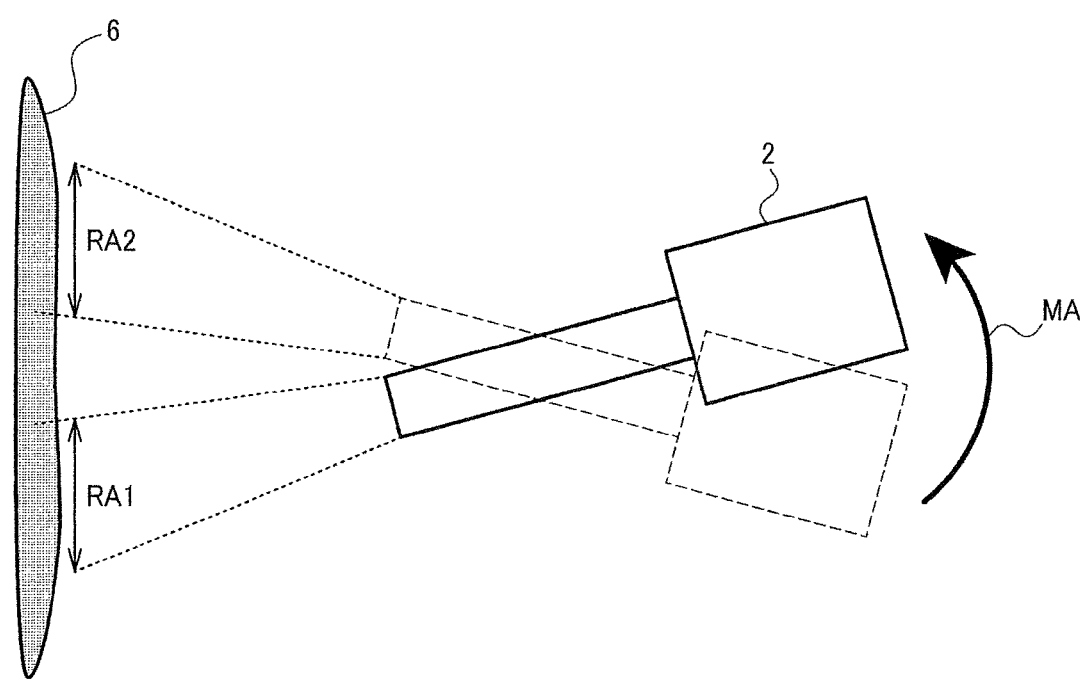
FIG. 4 illustrates a detailed configuration example of image sensor.
FIG. 5 is a view illustrating a vertical-to-optical axis motion.

The details of the image sensor 240 according to the second embodiment are described below with reference to FIG. 4. FIG. 4 is a partially enlarged view illustrating the image sensor 240. The image sensor 240 has a structure in which a plurality of pixels are arranged in a two-dimensional array, and R, G, and B color filters are disposed in a Bayer array on a pixel basis. The image sensor 240 may be an arbitrary image sensor other than an image sensor having a Bayer color filter array (see FIG. 4), such as an image sensor that utilizes a complementary color filter, a stacked image sensor that is designed so that each pixel can receive light having a different wavelength without using a color filter, and a monochrome image sensor that does not utilize a color filter, as long as the object can be captured to obtain an image.

The processing section 300 includes an A/D conversion section 310, a pre-processing section 320, an image processing section 330, a motion amount calculation section 340, a focus control section 350, and a control section 360. The A/D conversion section 310 converts analog signals sequentially output from the image sensor 240 into a digital image, and sequentially outputs the digital image to the pre-processing section 320. The pre-processing section 320 performs image processing (e.g., white balance process and interpolation process (demosaicing process (i.e., a process that generates an RGB image from a Bayer image)) on the image output from the A/D conversion section 310, and sequentially outputs the resulting image to the image processing section 330, the motion amount calculation section 340, and the focus control section 350. The image processing section 330 performs image processing (e.g., color conversion process, grayscale transformation process, edge enhancement process, scaling process, and noise reduction process) on the image output from the pre-processing section 320, and sequentially outputs the resulting image to the display section 400. The motion amount calculation section 340 calculates the inter-frame motion amount based on the image output from the pre-processing section 320, and outputs the calculated motion amount to the focus control section 350. The details of the motion amount calculation section 340 are described later. The focus control section 350 performs a control process that starts or stops the focus operation based on the motion amount output from the motion amount calculation section 340, and drives the focus lens driver section 220 during the focus operation so as to bring the object into focus. The details of the focus control section 350 are described later. The display section 400 is a liquid crystal monitor, for example. The display section 400 displays the image sequentially output from the image processing section 330.

The control section 360 is bidirectionally connected to the external I/F section 500, the image processing section 330, the focus control section 350, the image sensor 240, and the like, and exchanges a control signal with the external I/F section 500, the image processing section 330, the focus control section 350, the image sensor 240, and the like. The external I/F section 500 is an interface that allows the user to perform an input operation on the endoscope apparatus, for example. The external OF section 500 includes a setting button for setting the position and the size of the AF area, an adjustment button for adjusting the image processing parameters, and the like.

2.2. Motion Amount Calculation Section

The details of the motion amount calculation section 340 are described below. The motion amount calculation section 340 calculates the movement of the area of interest on the object (FIG. 5) to be a vertical-to-optical axis motion amount, and calculates a change in the distance between the object and the imaging section 200 (FIG. 6) to be a horizontal-to-optical axis motion amount, based on the image output from the pre-processing section 320. The team "vertical-to-optical axis motion amount" used herein refers to an amount that represents a change in position of the area of interest (field of view or imaging range) within the image in the upward, downward, rightward, and leftward directions. The term "horizontal-to-optical axis motion amount" used herein refers to an amount that represents a relative change in position with respect to the imaging section 200 and the object in the depth direction (i.e., the direction along the optical axis). Although an example in which the motion amount refers to both the vertical-to-optical axis motion amount and the horizontal-to-optical axis motion amount is described below, only one of the vertical-to-optical axis motion amount and the horizontal-to-optical axis motion amount may be used as the motion amount. Although an example in which the motion amount calculation section 340 processes only the G signals of the image output from the pre-processing section 320 is described below, various modifications may be appropriately made, such as a modification in which the motion amount calculation section 340 processes a brightness signal calculated from the RGB signals.

Figure 7:
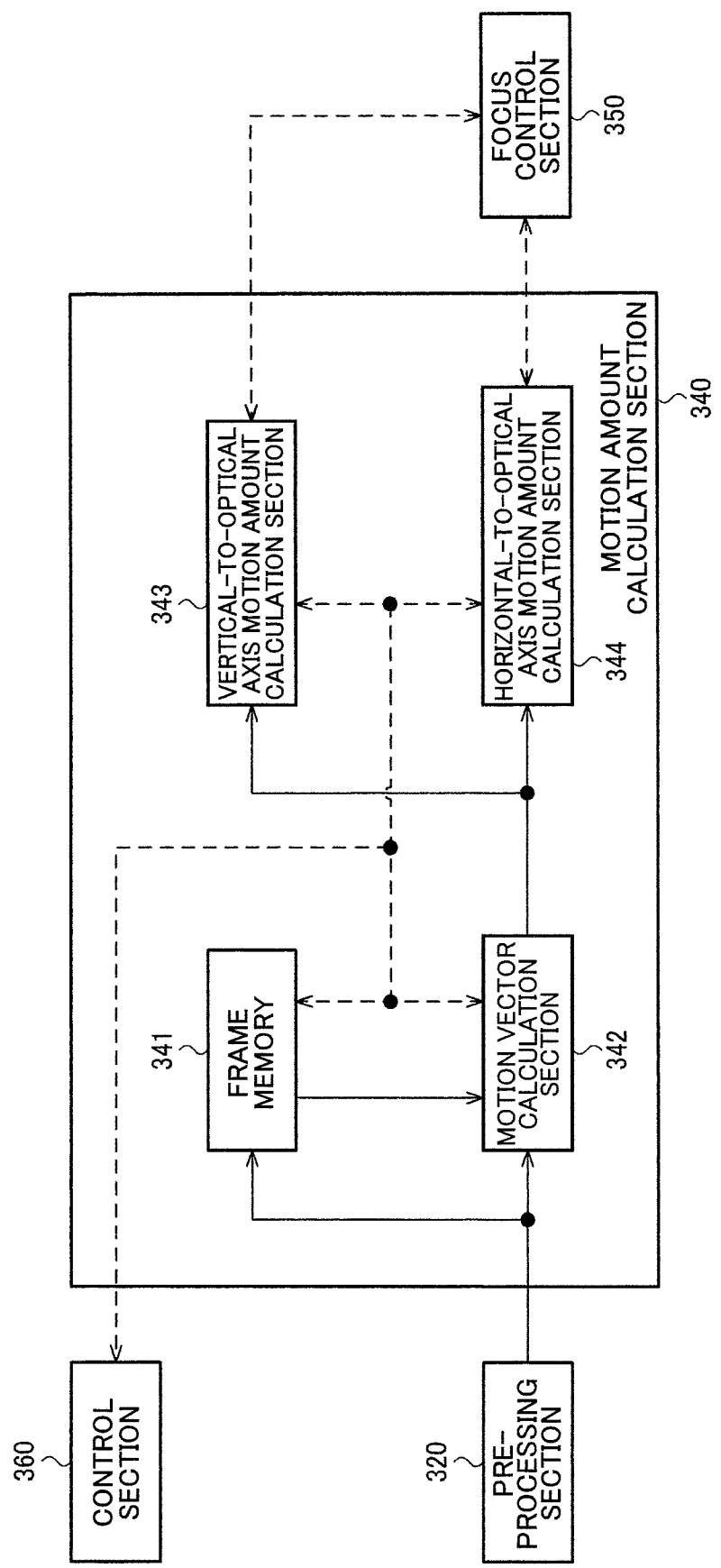
FIG. 7 illustrates a detailed configuration example of a motion amount calculation section.

FIG. 7 illustrates a detailed configuration example of the motion amount calculation section 340. The motion amount calculation section 340 includes a frame memory 341, a motion vector calculation section 342, a vertical-to-optical axis motion amount calculation section 343, and a horizontal-to-optical axis motion amount calculation section 344.

Figure 8:
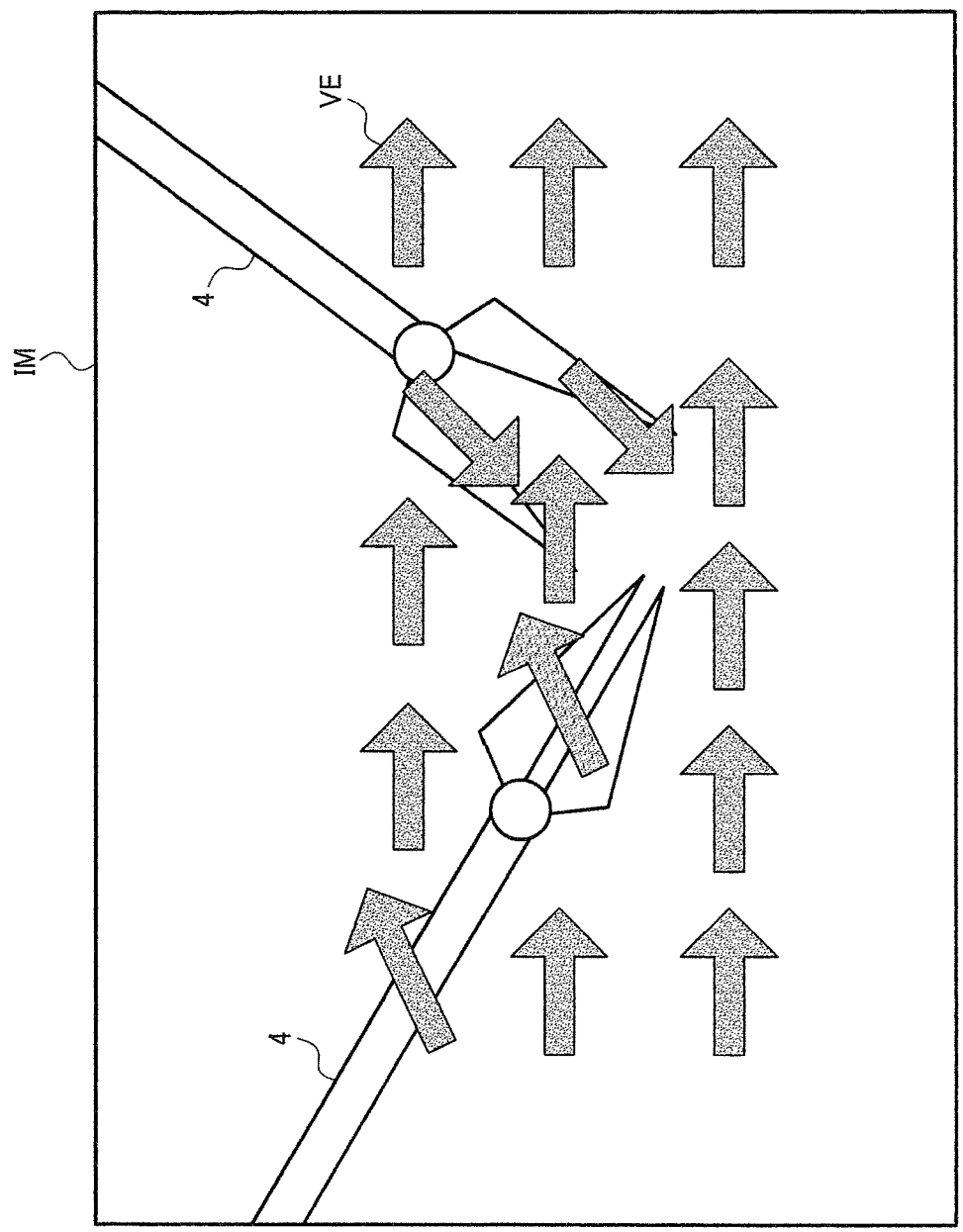
FIG. 8 illustrates an example of a local motion vector.

The frame memory 341 is a memory that temporarily stores the image output from the pre-processing section 320. The frame memory 341 subjects the image output from the pre-processing section 320 to a frame delay, and outputs the image to the motion vector calculation section 342. The motion vector calculation section 342 calculates the motion vector with respect to the image (i.e., the image that corresponds to the current frame) output from the pre-processing section 320, and the image (i.e., the image that corresponds to the previous frame) output from the frame memory 341 that has been subjected to a frame delay. The motion vector is calculated based on the image that corresponds to the current frame. More specifically, a local motion vector VE is calculated at a plurality of points within an image IM (see FIG. 8). The motion vector is calculated using a block matching method or a gradient method known in the art, for example. Although FIG. 8 illustrates an example in which the motion vector VE is calculated at a plurality of points that are set at equal intervals within the image IM, the motion vector may be calculated in another way. Various modifications may be appropriately made, such as a modification in which the motion vector is calculated at each pixel of the image.

The vertical-to-optical axis motion amount calculation section 343 calculates the vertical-to-optical axis motion amount MV (vertical-to-optical axis motion vector) based on the motion vector $v_i$ (i=0 to M−1) output from the motion vector calculation section 342. Specifically, the vertical-to-optical axis motion amount calculation section 343 calculates the vertical-to-optical axis motion amount MV using the following expression (1).

$$MV = \frac{\sum_{i=0}^{M-1} v_i}{M} \tag{1}$$

M is the total number of local motion vectors (M=15) in the example illustrated in FIG. 8). The M motion vectors are averaged to calculate the global motion amount over the entire image to be the vertical-to-optical axis motion amount MV.

Note that the vertical-to-optical axis motion amount MV may be calculated as described below. A first modification determines whether or not each motion vector (determination target motion vector) has a correlation with the peripheral motion vector, and calculates the vertical-to-optical axis motion amount MV from only the motion vectors that have been determined to have a correlation with the peripheral motion vector. Specifically, the vertical-to-optical axis motion amount MV is calculated using the following expressions (2) and (3).

$$MV = \frac{\sum_{i=0}^{M-1} v_i \cdot c_i}{\sum_{i=0}^{M-1} c_i} \tag{2}$$

$$c_i = \begin{cases} 0 & \text{Motion vector does not have correlation with peripheral motion vector} \\ 1 & \text{Motion vector does have correlation with peripheral motion vector} \end{cases} \tag{3}$$

The correlation between the determination target motion vector and the peripheral motion vector is represented by the magnitude f the difference between the determination target motion vector and the peripheral motion vector, for example. It is determined that the determination target motion vector has a correlation with the peripheral motion vector when the magnitude of the difference is less than a given threshold value, and it is determined that the determination target motion vector does not have a correlation with the peripheral motion vector when the magnitude of the difference is equal to or larger than the given threshold value. For example, when four peripheral motion vectors are situated around the determination target motion vector in the upward, downward, rightward, and leftward directions, the threshold value determination process is performed with respect to each peripheral motion vector. For example, it may be determined that the determination target motion vector does not have a correlation with the peripheral motion vector when the magnitude of the difference is equal to or larger than the given threshold value with respect to at least one peripheral motion vector among the four peripheral motion vectors, or it may be determined that the determination target motion vector does not have a correlation with the peripheral motion vector when the magnitude of the difference is equal to or larger than the given threshold value with respect to two peripheral motion vectors, or three or more peripheral motion vectors, among the four peripheral motion vectors. When none of the M motion vectors have been determined to have a correlation with the peripheral motion vector, it is determined that a motion vertical to the optical axis has not occurred, and the subsequent process is performed on the assumption that the vertical-to-optical axis motion amount MV is "0".

The motion vector $v_i$ includes a motion vector due to the movement of the area of interest on the object, and a motion vector due to disturbance (e.g., manipulation of forceps during the procedure). The motion vector due to disturbance does not have a correlation with the peripheral motion vector. The vertical-to-optical axis motion amount MV can be calculated with high accuracy (i.e., the vertical-to-optical axis motion amount MV between the tissue and the imaging section can be calculated to exclude disturbance due to the treatment tool) by excluding the motion vector due to disturbance based on the presence or absence of a correlation between the determination target motion vector and the peripheral motion vector (see the expressions (2) and (3)).

A second modification generates a two-dimensional histogram with respect to direction and magnitude (see FIG. 9) from the M motion vectors, and calculates the vertical-to-optical axis motion amount MV from the two-dimensional histogram. In the example illustrated in FIG. 9, the direction of the motion vector is quantized into 8 levels (i.e., a direction that corresponds to the magnitude "0", and eight directions other than the direction that corresponds to the magnitude "0"), and the magnitude of the motion vector is quantized into 11 levels (represented by the number of pixels on an 8 pixel basis). The vertical-to-optical axis motion amount MV is calculated from the motion vector that corresponds to the bin in which the frequency becomes a maximum in the two-dimensional histogram. In the example illustrated in FIG. 9, the motion vector that corresponds to the bin that corresponds to the rightward direction and the magnitude 8 to 15 has a maximum frequency of 11, and the vertical-to-optical axis motion amount MV is calculated from that motion vector. In this case, the median value (e.g., 12) may be used as the magnitude, for example.

The two-dimensional histogram illustrated in FIG. 9 was generated based on the fifteen motion vectors illustrated in FIG. 8. In the example illustrated in FIG. 8, tissue is captured to occupy the majority of the image IM, and the motion vectors (i.e., the motion vectors in the rightward direction) of the tissue are almost uniform with respect to the movement (motion) in the area of interest on the object. Therefore, when a movement has occurred in the area of interest on the object, most of the motion vectors (i.e., eleven motion vectors among the fifteen motion vectors) are similar to each other as to the direction and the magnitude. These motion vectors of the tissue correspond to the bin that is included in the histogram illustrated in FIG. 9 and has a frequency of 11. On the other hand, the number of motion vectors (i.e., the motion vectors in the upper right direction, and the motion vectors in the lower left direction) due to disturbance (e.g., treatment tool) is small (i.e., four motion vectors among the fifteen (M) motion vectors). The motion vectors due to disturbance differ from the motion vectors of the tissue as to the direction and the magnitude. The motion vectors due to disturbance correspond to the bins that are included in the histogram illustrated in FIG. 9 and have a frequency of 2. Specifically, the vertical-to-optical axis motion amount MV can be calculated while excluding the effect of disturbance by utilizing the bin that is included in the two-dimensional histogram and has the maximum frequency.

Figure 10:
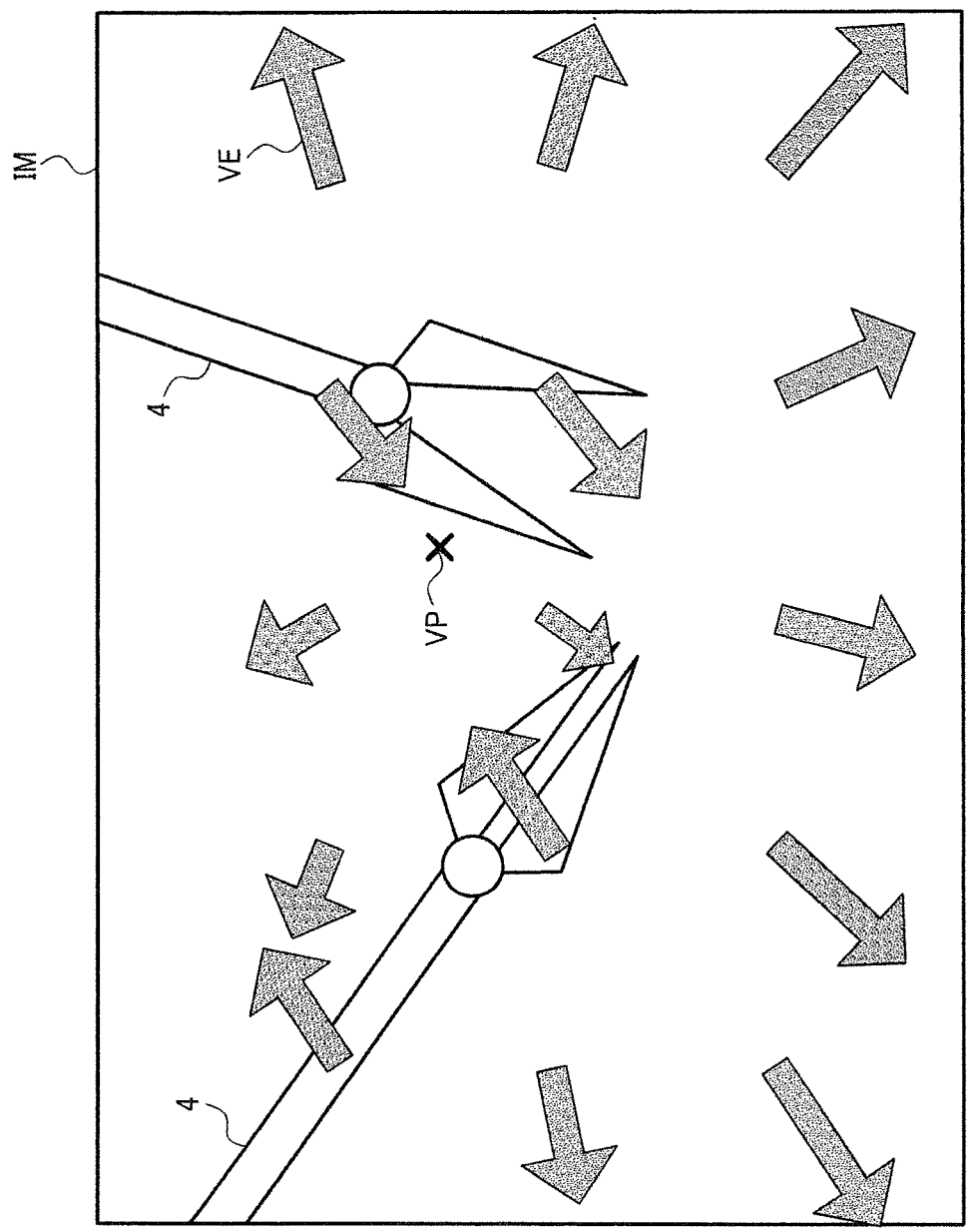
FIG. 10 illustrates an example of a local motion vector.

The horizontal-to-optical axis motion amount calculation section 344 calculates the horizontal-to-optical axis motion amount MH based on the motion vector output from the motion vector calculation section 342. FIG. 10 illustrates an example of the local motion vectors VE when a horizontal-to-optical axis motion has occurred. FIG. 10 illustrates an example of the local motion vectors VE when the imaging section moves away from the object. When a horizontal-to-optical axis motion has occurred, straight lines obtained by extending the motion vectors ideally converge at one point (vanishing point VP). In the example illustrated in FIG. 10, extensions of the motion vectors do not converge at one point due to disturbance (i.e., treatment tool), but ideally converge at one point when the disturbance is removed. It is determined that the imaging section moves away from the object when the vanishing point exists on the side on which the start point of each motion vector is extended. In this case, the motion vector extends outward from the vanishing point. It is determined that the imaging section moves closer to the object when the vanishing point exists on the side on which the end point of each motion vector is extended. In this case, the motion vector extends (inward) toward the vanishing point. Since the motion vector with respect to the previous frame is calculated based on the current frame (see above), the motion vector extends outward/inward with respect to the movement of the imaging section that moves away from/closer to the object. Note that the motion vector with respect to the current frame may be calculated based on the previous frame, and the motion vector may extend inward/outward with respect to the movement of the imaging section that moves away from/closer to the object.

Figure 11:
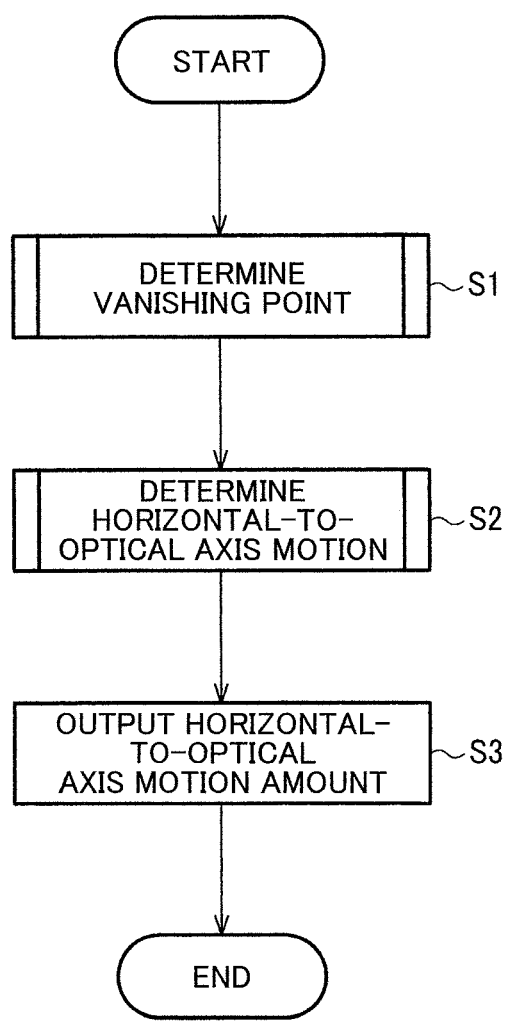
FIG. 11 is a flowchart illustrating a process that calculates a horizontal-to-optical axis motion amount.

FIG. 11 is a flowchart illustrating the process that calculates the horizontal-to-optical axis motion amount MH. The vanishing point is determined (S1). When a horizontal-to-optical axis motion has occurred, the distance between a straight line obtained by extending the motion vector and the vanishing point is ideally "0". However, since the motion vector quantization accuracy is limited, or disturbance due to a treatment tool or the like occurs, the distance between a straight line obtained by extending the motion vector and the vanishing point does not become "0". Therefore, a point at which the sum of the distance from a straight line obtained by extending the M motion vector $v_i$ (i=0 to M−1) becomes a minimum is determined to be the vanishing point.

Whether or not a horizontal-to-optical axis motion has occurred is determined. When it has been determined that a horizontal-to-optical axis motion has occurred, whether the horizontal-to-optical axis motion is a motion that moves away from the object, or a motion that moves closer to the object, is determined (S2). Whether or not a horizontal-to-optical axis motion has occurred is determined based on the reliability of the vanishing point. It is considered that the reliability of the vanishing point is high when the sum of the distances (see above) is small. Therefore, it is determined that the reliability of the vanishing point is high (i.e., a horizontal-to-optical axis motion has occurred) when the sum of the distances is equal to or less than a given threshold value. On the other hand, it is determined that the reliability of the vanishing point is low (i.e., a horizontal-to-optical axis motion has not occurred) when the sum of the distances is larger than the given threshold value. When it has been determined that a horizontal-to-optical axis motion has occurred, the direction of the horizontal-to-optical axis motion (i.e., whether the horizontal-to-optical axis motion is a motion that moves away from the object, or a motion that moves closer to the object) is determined based on the direction of each motion vector (i.e., whether or not the direction of each motion vector intersects the vanishing point). When it is impossible to determine whether the horizontal-to-optical axis motion is a motion that moves away from the object, or a motion that moves closer to the object, it is determined that a horizontal-to-optical axis motion has not occurred.

The horizontal-to-optical axis motion amount MH (see the following expression (4)) is output based on the determination results obtained in the step S2 (S3).

$$MH = \begin{cases} -1 & \text{Motion that moves away from object} \\ 0 & \text{No horizontal-to-optical axis motion} \\ +1 & \text{Motion that moves closer to object} \end{cases} \quad (4)$$

In the step S2, whether the horizontal-to-optical axis motion is a motion that moves away from the object, or a motion that moves closer to the object, is determined as described below, for example Specifically, whether the horizontal-to-optical axis motion is a motion that moves away from the object, or a motion that moves closer to the object, is determined using the angle $(\arg(v_i)-\arg(l_i))$ formed by the motion vector $v_i$ (i=0 to M−1) and a vector $l_i$ that corresponds to the motion vector $v_i$. The vector $l_i$ starts at the start point SP of the motion vector $v_i$, and ends at the vanishing point VP. arg(x) is a function that returns the argument of a vector x.

Figure 13:
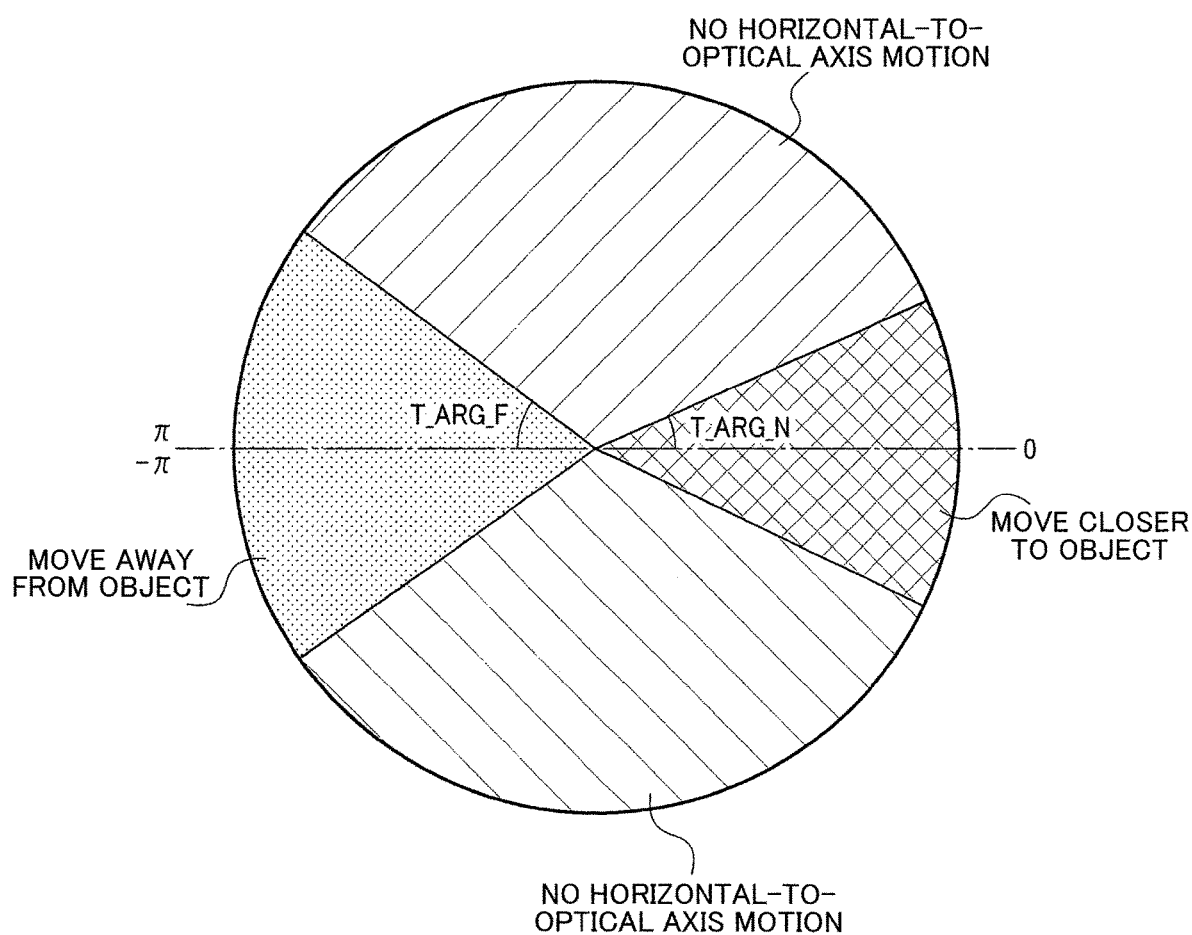
FIG. 13 is a view illustrating a process that determines the direction of a horizontal-to-optical axis motion.

More specifically, the M motion vectors are classified using the following expression (5). FIG. 13 is a schematic view illustrating the expression (5). The maximum classification result with respect to the M motion vectors is determined to be the determination result with respect to the horizontal-to-optical axis motion. When a plurality of maximum classification results have been obtained, it is determined that a horizontal-to-optical axis motion has not occurred. In the example illustrated in FIG. 10, the motion vectors (eleven motion vectors) of the tissue are classified as a motion that moves away from the object, and the motion vectors (four motion vectors) of the treatment tool are classified as a motion that moves closer to the object, or no motion. Therefore, it is determined that the horizontal-to-optical axis motion is a motion that moves away from the object.

$\arg(v_i)-\arg(l_i) \leq -\pi + T\_ARG\_F$ or $\pi - T\_ARG\_F \leq (v_i)-\arg(l_i) \Rightarrow$ Motion that moves away from object $|\arg(v_i)-\arg(l_i)| \leq T\_ARG\_N \Rightarrow$ Motion that moves closer to object $\Rightarrow$ otherwise No horizontal-to-optical axis motion (5)

T_ARG_F is a threshold value that corresponds to a motion that moves away from the object. T_ARG_F is a threshold value that corresponds to a motion that moves closer to the object. Since the direction of the motion vector is opposite to the vanishing point when the horizontal-to-optical axis motion is a motion that moves away from the object, $\arg(v_i)-\arg(l_i)$ approaches $\pm\pi$. Since the direction of the motion vector intersects the vanishing point when the horizontal-to-optical axis motion is a motion that moves closer to the object, $\arg(v_i)-\arg(l_i)$ approaches "0". Therefore, the presence or absence and the direction of the horizontal-to-optical axis motion can be determined using the expression (5).

Note that whether the horizontal-to-optical axis motion is a motion that moves away from the object, or a motion that moves closer to the object, may be determined as described below. Specifically, whether the horizontal-to-optical axis motion is a motion that moves away from the object, or a motion that moves closer to the object, may be determined using the inner product of the motion vector $v_i$ and the vector $l_i$ (see the following expressions (6) and (7)).

$$\frac{\sum_{i=0}^{M-1} \frac{v_i \cdot l_i}{|v_i||l_i|}}{M} \leq T\_PRO\_F \Rightarrow \text{Motion that moves away from object} \quad (6)$$

$$T\_PRO\_N \leq \frac{\sum_{i=0}^{M-1} \frac{v_i \cdot l_i}{|v_i||l_i|}}{M} \Rightarrow \text{Motion that moves closer to object}$$

otherwise $\Rightarrow$ No horizontal-to-optical axis motion $-1 \leq T\_PRO\_F < 0 < T\_PRO\_N \leq +1$ (7)

$v_i \cdot l_i$ is the inner product of the motion vector $v_i$ and the vector $l_i$. |x| is the magnitude of a vector x. T_PRO_F is a threshold value with respect to the inner product that corresponds to a motion that moves away from the object. T_PRO_N is a threshold value with respect to the inner product that corresponds to a motion that moves closer to the object. Since the direction of the motion vector is opposite to the vanishing point when the horizontal-to-optical axis motion is a motion that moves away from the object, $(v_i \cdot l_i)/|v_i||l_i|$ approaches "−1". Since the direction of the motion vector intersects the vanishing point when the horizontal-to-optical axis motion is a motion that moves closer to the object, $(v_i \cdot l_i)/|v_i||l_i|$ approaches "+1". Therefore, the presence or absence and the direction of the horizontal-to-optical axis motion can be determined using the expressions (6) and (7).

Note that the vertical-to-optical axis motion amount may also be calculated as described below. Specifically, whether or not each motion vector (determination target motion vector) has a correlation with the peripheral motion vector may be determined, and the horizontal-to-optical axis motion amount MH may be calculated from the motion vectors that have been determined to have a correlation with the peripheral motion vector (see the expressions (2) and (3)). As illustrated in FIG. 10, when a horizontal-to-optical axis motion has occurred, the directions of the peripheral motion vectors differ to some extent in the tissue area (that has a high correlation). Therefore, the correlation determination threshold value used for a horizontal-to-optical axis motion may be set to be larger than the correlation determination threshold value used for a vertical-to-optical axis motion.

Although an example in which the horizontal-to-optical axis motion amount is calculated based on the motion vector has been described above, the horizontal-to-optical axis motion amount may be calculated in another way. For example, the horizontal-to-optical axis motion amount may be calculated from the image using a rotation-invariant phase-only correlation (RIPOC) method. In this case, it is determined that the horizontal-to-optical axis motion is a motion that moves away from the object when the image stored in the frame memory is larger than the image acquired at the current timing, it is determined that the horizontal-to-optical axis motion is a motion that moves closer to the object when the image stored in the frame memory is smaller than the image acquired at the current timing, and it is determined that a horizontal-to-optical axis motion has not occurred when the image stored in the frame memory is equal in size to the image acquired at the current timing.

2.3. Focus Control Section

The details of the focus control process (AF control process) performed by the focus control section 350 are described below.

Figure 14:
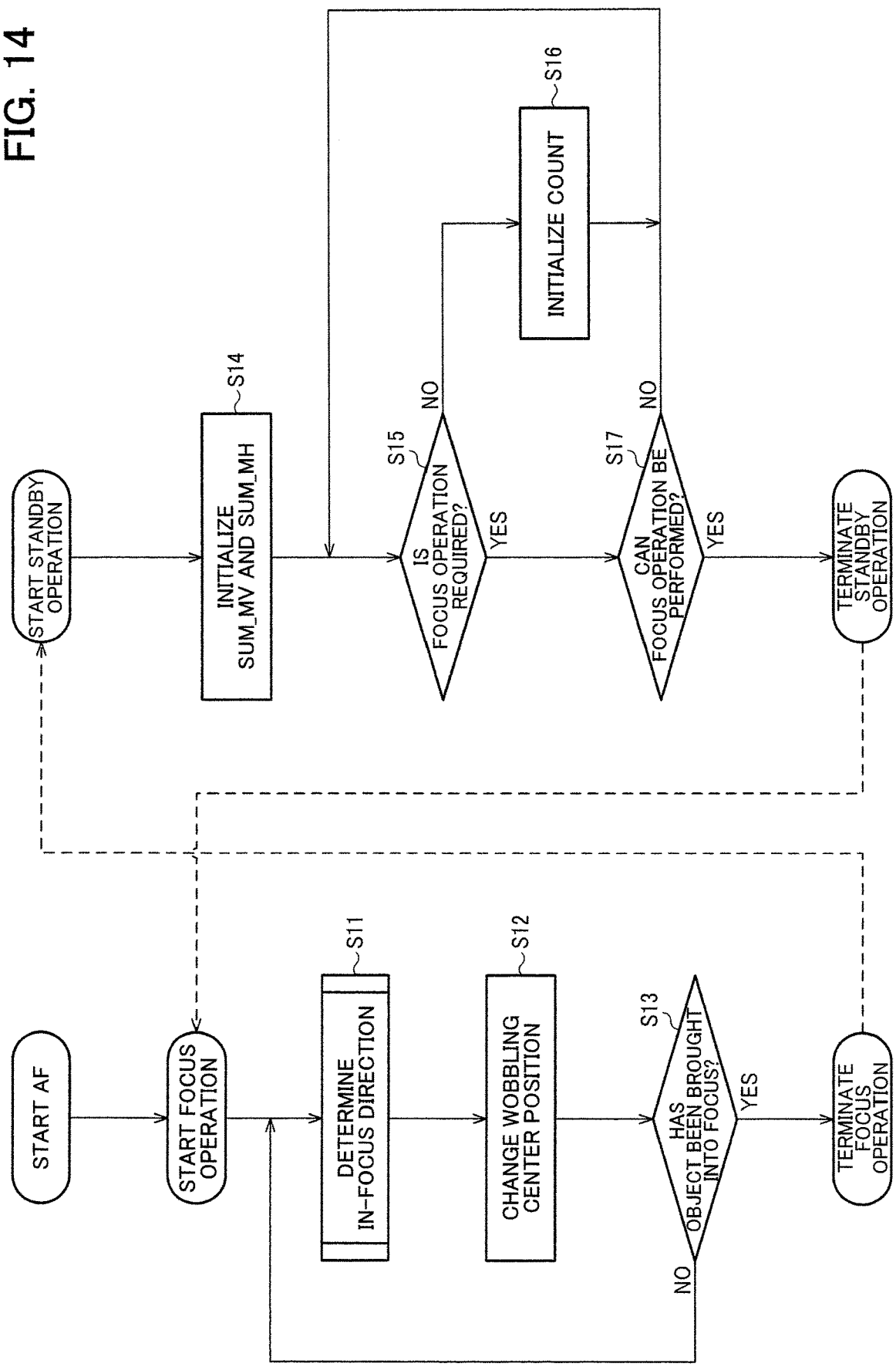
FIG. 14 is a flowchart illustrating a focus control process.

FIG. 14 is a flowchart illustrating the focus control process. The focus operation described above corresponds to the steps S11 to S13 illustrated in FIG. 14.

The focus control section 350 determines the in-focus direction (S11). More specifically, the focus control section 350 causes the focus lens 210 to make a wobbling motion in synchronization with the acquisition timing of the image that is sequentially output from the A/D conversion section 310. The term "wobbling motion" used herein refers to a state in which the focus lens 210 moves (wobbles) in the forward-backward direction so that the in-focus object plane position moves (wobbles) in the forward-backward direction (infinity-near direction). A plurality of images that differ in the in-focus object plane position are captured during the wobbling motion. For example, the focus lens 210 is moved to the wobbling center, and three points around the wobbling center. In this case, images are sequentially captured at the three points. The focus control section 350 determines the in-focus direction using a known method based on the images acquired during the wobbling motion, for example. For example, the contrast values of a plurality of images captured during the wobbling motion are calculated, and the in-focus direction is determined from the calculated contrast values. For example, when a higher contrast value is obtained when the in-focus object plane position is moved to the infinity side, the direction in which the in-focus object plane position is moved to the infinity side is the in-focus direction.

The focus control section 350 changes the wobbling center position based on the in-focus direction determined by the step S11 (S12). More specifically, the in-focus direction determined by the step S11 is the direction in which the in-focus object plane position is situated on the near (near point) side with respect to the image sensor 240, or the direction in which the in-focus object plane position is situated on the infinity (far point) side with respect to the image sensor 240. The wobbling center is moved to the near side when the in-focus direction is the direction in which the in-focus object plane position is situated on the near side, and is moved to the infinity side when the in-focus direction is the direction in which the in-focus object plane position is situated on the infinity side.

The focus control section 350 determines whether or not the object has been brought into focus (S13). The focus control section 350 determines whether or not the object has been brought into focus by performing a known in-focus determination process or the like. For example, whether or not the object has been brought into focus may be determined based on the contrast value of the image, or may be determined based on whether or not the wobbling center is moved. When the focus control section 350 has determined that the object has not been brought into focus, the focus control section 350 repeats the steps S11 to S13 to gradually bring the wobbling center position closer to the object (gradually bring the object into focus). When the focus control section 350 has determined that the object has been brought into focus, the focus control section 350 stops causing the focus lens 210 to make a wobbling motion, and terminates the focus operation. After completion of the focus operation, the focus control section 350 performs a standby operation. The focus control section 350 does not perform the focus operation (does not move the focus lens 210) during the standby operation. For example, the focus control section 350 stops the focus lens 210 at the position of the focus lens 210 when it has been determined that the object has been brought into focus in the step S13.

When the standby operation has started, the focus control section 350 initializes values SUM_MV and SUM_MH (S14). The values SUM_MV and SUM_MH are used to determine whether or not the focus operation is required in the step S15 described later.

The focus control section 350 determines whether or not the focus operation is required based on the vertical-to-optical axis motion amount MV and the horizontal-to-optical axis motion amount MH (S15). When the focus control section 350 has determined that the focus operation is not required, the focus control section 350 initializes a value COUNT (S16), and performs the step S15 in synchronization with the next image acquisition timing. The value COUNT is used to determine whether or not it is possible to perform the focus operation (as described later). When the focus control section 350 has determined that the focus operation is required, the focus control section 350 determines whether or not it is possible to perform the focus operation (S17). When the focus control section 350 has determined that it is impossible to perform the focus operation, the focus control section 350 performs the step S15 in synchronization with the next image acquisition timing. When the focus control section 350 has determined that it is possible to perform the focus operation, the focus control section 350 terminates the standby operation, and starts the focus operation (performs the step S11). The details of the determination process that determines whether or not the focus operation is required (S15), and the determination process that determines whether or not it is possible to perform the focus operation (S17), are described below.

The determination process that determines whether or not the focus operation is required (S15), is described below. The focus operation is required when the focus state of the object has changed from an in-focus state to an out-of-focus state (i.e., when the object has become out of focus). The focus state of the object changes from an in-focus state to an out-of-focus state when the user has moved the area of interest on the object by operating the endoscope, or when the user has changed the distance from the imaging section to the object by operating the endoscope. It is determined that the focus operation is required when it has been detected that the user has moved the area of interest on the object by operating the endoscope, or changed the distance from the imaging section to the object by operating the endoscope, based on the vertical-to-optical axis motion amount MV and the horizontal-to-optical axis motion amount MH. When it has not been detected that the user has moved the area of interest on the object by operating the endoscope, or changed the distance from the imaging section to the object by operating the endoscope, the step S16 is performed, and the step S15 is performed in synchronization with the next image acquisition timing.

When the user has moved the area of interest on the object, the vertical-to-optical axis motion amount $MV_j$ is detected between the frame before the user moves the area of interest on the object, and the frame after the user has moved the area of interest on the object. When the absolute value of the value SUM_MV obtained by accumulating the vertical-to-optical axis motion amount $MV_j$ over N frames (wherein N is a natural number equal to or larger than 3) has exceeded a given threshold value T_MV, it is determined that the focus operation is required since the focus state of the object has changed from an in-focus state to an out-of-focus state due to the movement of the area of interest on the object. More specifically, the determination process is performed using the following expressions (8) and (9). Note that j is the frame number, and "j=0" corresponds to the first frame after the standby operation has been started (or the reference frame after the standby operation has been started). "j=N−1" corresponds to the current frame.

$$\text{SUM\_MV} = \sum_{j=0}^{N-1} MV_j \tag{8}$$

|SUM_MV| > T_MV ⟹ Focus operation is required (9)
|SUM_MV| ≤ T_MV ⟹ Focus operation is not required The value SUM_MV is a value (two-dimensional vector) that is obtained by accumulating the vertical-to-optical axis motion amount $MV_j$, and includes a component in the upward-downward (vertical) direction and a component in the rightward-leftward (horizontal) direction (e.g., an x component and a y component within the image, or a component in the horizontal scan direction and a component in the vertical scan direction).

Note that whether or not the focus operation is required may be determined based on the value SUM_MV as described below. Specifically, when an endoscopic procedure is performed, tissue (e.g., internal organ) is observed in a folded state in the upward-downward direction. Therefore, even when the magnitude of the vector is identical, it is likely that the area of interest has been moved to a different internal organ, and the object becomes out of focus in the upward-downward direction as compared with the rightward-leftward direction. Therefore, it may be more easily determined that the focus operation is required when a vertical-to-optical axis motion has occurred in the upward-downward direction as compared with the case where a vertical-to-optical axis motion has occurred in the rightward-leftward direction. More specifically, the determination process is performed using the following expressions (10) and (11).

|SUM_MV_V|>T_MV_V or
|SUM_MV_H|>T_MV_H ⟹ Focus operation is required

|SUM_MV_V|≤T_MV_V and |SUM_MV_H|≤T_MV_H ⟹ Focus operation is not required (10)

$$T\_MV\_V < T\_MV\_H \tag{11}$$

Note that SUM_MV_V is a component of the value SUM_MV in the upward-downward direction, and SUM_MV_H is a component of the value SUM_MV in the rightward-leftward direction. T_MV_V is a threshold value with respect to the component SUM_MV_V in the upward-downward direction, and T_MV_H is a threshold value with respect to the component SUM_MV_H in the rightward-leftward direction. It is possible to more accurately determine the case where the focus operation is required, by performing the determination process using different threshold values with respect to the upward-downward direction and the rightward-leftward direction.

When the user has changed the distance between the endoscope and the object, the horizontal-to-optical axis motion amount $MH_j$ is detected between the frame before the user changes the distance between the endoscope and the object, and the frame after the user has changed the distance between the endoscope and the object. When the absolute value of the value SUM_MH obtained by accumulating the horizontal-to-optical axis motion amount $MH_j$ over N frames (wherein N is a natural number equal to or larger than 3) (from the first timing after the standby operation has been started, to the current timing) has exceeded a given threshold value T_MH, it is determined that the focus operation is required since the focus state of the object has changed from an in-focus state to an out-of-focus state due to the change in the distance to the object. More specifically, the determination process is performed using the following expressions (12) and (13). Note that j is the frame number, and "j=0" corresponds to the first frame after the standby operation has been started (or the reference frame after the standby operation has been started). "j=N−1" corresponds to the current frame.

$$\text{SUM\_MH} = \sum_{j=0}^{N-1} MH_j \tag{12}$$

|SUM_MH| > T_MH ⟹ Focus operation is required (13)
|SUM_MH| ≤ T_MH ⟹ Focus operation is not required Note that whether or not the focus operation is required may be determined based on the value SUM_MH as described below. Specifically, the threshold value T_MH may be changed corresponding to whether the horizontal-to-optical axis motion is a motion that moves closer to the object, or a motion that moves away from the object. The focus operation is required when the distance between the endoscope and the object falls outside the depth of field. Since the depth of field is shallower on the near side as compared with the infinity side with respect to the in-focus object plane position, it is likely that the object becomes out of focus when a horizontal-to-optical axis motion that moves closer to the object has occurred as compared with the case where a horizontal-to-optical axis motion that moves away from the object has occurred, even when the absolute value of the horizontal-to-optical axis motion amount is identical. Therefore, it may be more easily determined that the focus operation is required when a horizontal-to-optical axis motion that moves closer to the object has occurred as compared with the case where a horizontal-to-optical axis motion that moves away from the object has occurred. More specifically, the determination process is performed using the following expressions (14) to (16).

$$\text{SUM\_MH} < T\_MH\_F \text{ or SUM\_MH} > T\_MH\_N \Rightarrow \text{Focus operation is required}$$

$$T\_MH\_F \leq \text{SUM\_MH} \leq T\_MH\_N \Rightarrow \text{Focus operation is not required} \qquad (14)$$

$$T\_MH\_F < 0 < T\_MH\_N \qquad (15)$$

$$|T\_MH\_N| < |T\_MH\_F| \qquad (16)$$

Note that T_MH_N is a threshold value with respect to the value SUM_MH in the direction in which the imaging section moves closer to the object, and T_MH_F is a threshold value with respect to the value SUM_MH in the direction in which the imaging section moves away from the object. It is possible to more accurately determine the case where the focus operation is required, by performing the determination process using different threshold values with respect to the case where the imaging section moves closer to the object, and the case where the imaging section moves away from the object.

Figure 15:
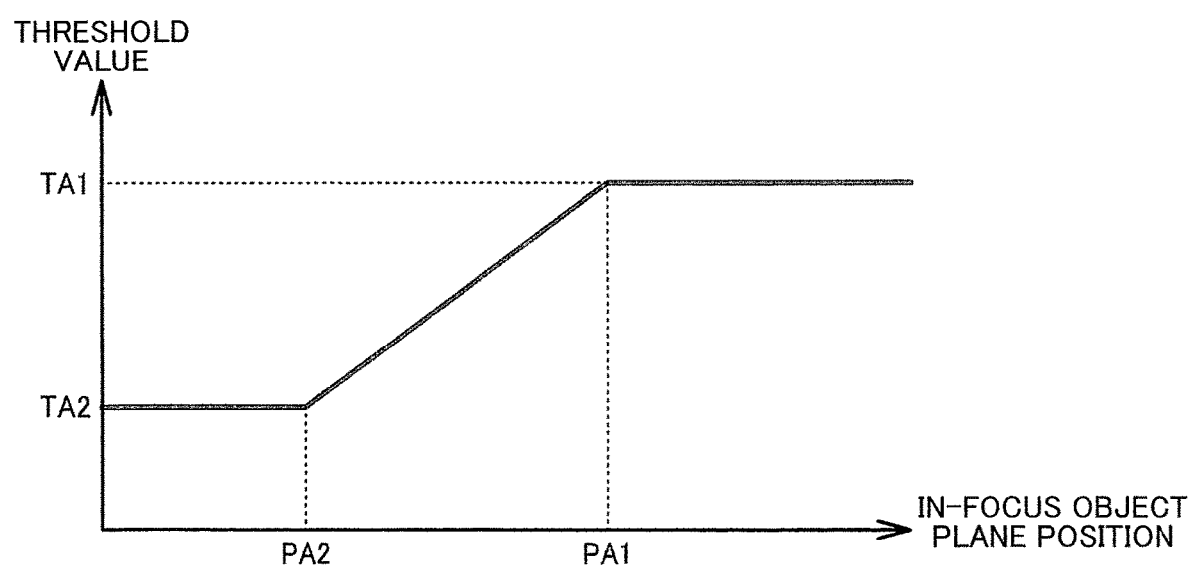
FIG. 15 illustrates an example in which a threshold value is set corresponding to an in-focus object plane position.

Although an example in which whether or not the focus operation is required is determined based on the vertical-to-optical axis motion amount and the horizontal-to-optical axis motion amount has been described above, whether or not the focus operation is required may be determined in another way. For example, the determination process may be performed further based on the in-focus object plane position. More specifically, since the depth of field is relatively shallow when the in-focus object plane position is situated on the near side with respect to the imaging section 200 as compared with the case where the in-focus object plane position is situated on the infinity side with respect to the imaging section 200, the object easily becomes out of focus even when the vertical-to-optical axis motion amount and the horizontal-to-optical axis motion amount are identical. Therefore, if the threshold value is set based on the case where the in-focus object plane position is situated relatively on the near side, an unnecessary focus operation may be performed when the in-focus object plane position is situated relatively on the infinity side. On the other hand, if the threshold value is set based on the case where the in-focus object plane position is situated relatively on the infinity side, the focus operation may not be performed when the in-focus object plane position is situated relatively on the near side even when the object is out of focus. Therefore, the threshold value may be set corresponding to the in-focus object plane position (see FIG. 15) so that it is more easily determined that the focus operation is required when the in-focus object plane position is situated relatively on the near side as compared with the case where the in-focus object plane position is situated relatively on the infinity side. In the example illustrated in FIG. 15, the threshold value is set to TA1 when the in-focus object plane position is set to PA1, and is set to TA2 when the in-focus object plane position is set to PA2 (PA1>PA2 (i.e., the in-focus object plane position PA1 is situated on the infinity side), and TA1>TA2). Note that the threshold value need not necessarily be set as illustrated in FIG. 15. The threshold value may be set in an arbitrary way as long as it is more easily determined that the focus operation is required when the in-focus object plane position is situated relatively on the near side as compared with the case where the in-focus object plane position is situated relatively on the infinity side.

Although an example in which the motion amount is accumulated over N frames from the first timing after the standby operation has been started, to the current timing (i.e., N increases by one as the current frame number increases by one), has been described above, the motion amount may be accumulated in another way. Specifically, since the motion vector has finite precision, and includes an error, it may be erroneously determined that the focus operation is required when the motion vector is accumulated for a long time due to the accumulation of the error. Therefore, the motion amount may be accumulated from the current frame up to the Nth previous frame (N=K (wherein K is a natural number equal to or larger than 3). In this case, N=K is a given number (e.g., fixed number). Specifically, N=K basically does not change even when the current frame number has increased by one.

The determination process that determines whether or not the focus operation can be performed (S17), is described below. For example, when the focus operation is performed immediately after it has been determined that the focus operation is required while the endoscope is being operated (e.g., while the area of interest is being moved), the focus operation may be completed before completion of the operation of the endoscope, and the object may be out of focus after completion of the operation of the endoscope. In this case, since the focus operation is performed while the user is operating the endoscope, the usability of the endoscope may be impaired. Therefore, the focus operation is performed after it has been determined that the focus operation is required in the step S15, and it has been determined that the movement of the area of interest and a change in the distance to the object do not occur.

Figure 16:
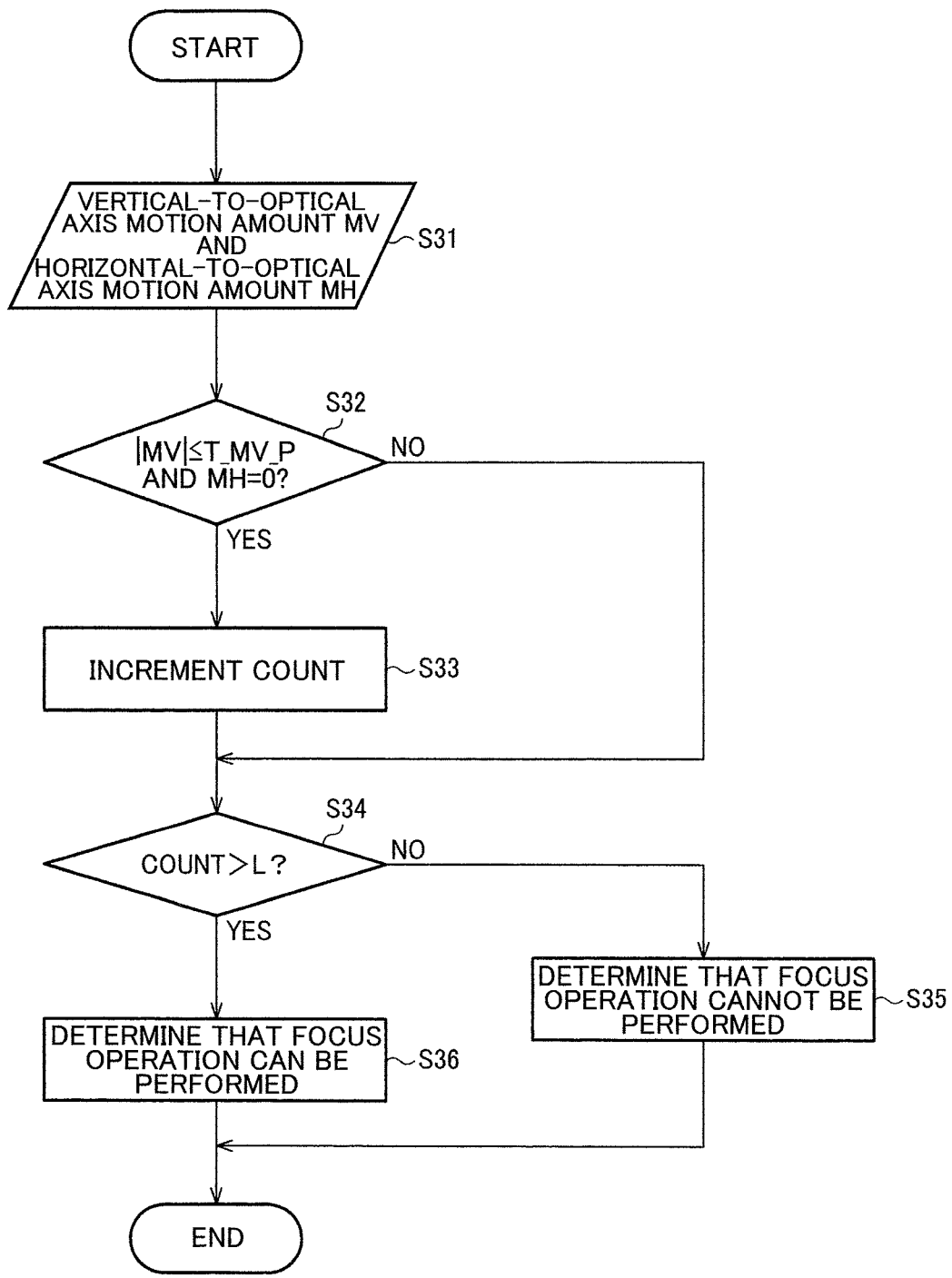
FIG. 16 is a flowchart illustrating a process that determines whether or not a focus operation can be performed.

FIG. 16 is a detailed flowchart illustrating the process that determines whether or not the focus operation can be performed. Whether or not the vertical-to-optical axis motion amount MV and the horizontal-to-optical axis motion amount MH are equal to or smaller than a given value is determined on a frame basis. Specifically, whether or not an inter-frame motion has not occurred, or has occurred to only a small extent, is determined (S32). More specifically, the determination process is performed using the following expression (17).

$$|MV| \leq T\_MV\_P \text{ and } MH=0 \Rightarrow \text{Motion has not occurred}$$

$$|MV| > T\_MV\_P \text{ or } MH \neq \Rightarrow \text{Motion has occurred} \qquad (17)$$

Note that T_MV_P is a threshold value with respect to the vertical-to-optical axis motion amount MV.

When it has been determined that a motion has not occurred in the step S32, a value COUNT that is used for the determination process is incremented (S33). When it has been determined that a motion has occurred in the step S32, a step S34 is performed.

Whether or not the value COUNT is larger than L (frames) (wherein L is a natural number equal to or larger than 3) is determined (S34). When the value COUNT is larger than L (frames), it is determined that the focus operation can be performed (S36), and the focus operation (S11 to S13 in FIG. 14) is performed. When the value COUNT is equal to or smaller than L (frames), it is determined that the focus operation cannot be performed (S35), and whether or not the focus operation is required is determined (S15 in FIG. 14) with respect to the next frame.

It is possible to perform the focus operation when a vertical-to-optical axis motion and a horizontal-to-optical axis motion have not occurred over a number of frames equal to or larger than a given number of frames, and suppress a situation in which the focus operation is unnecessarily performed, by determining whether or not the focus operation can be performed as described above.

According to the second embodiment, reflected light from the object is captured as an image using the imaging section that can perform the focus operation. The relative motion amount with respect to the imaging section and the object is calculated from the image. When the net motion amount obtained by accumulating the motion amount over a plurality of frames has exceeded a given threshold value, it is determined that the focus operation is required, and the imaging section performs the focus operation. Since the focus operation is performed when the motion amount obtained by accumulating the motion amount over a plurality of frames has exceeded a given amount, it is possible to implement an AF control process that performs the focus operation when the object has become out of focus even when the motion is slow, and does not perform the focus operation when an unintentional momentary motion has occurred.

According to the second embodiment, the focus control section 350 (processor) performs a focus feasibility determination process (S17) that determines (expression (17)) whether or not there have been L frames (wherein L is a natural number equal to or larger than 3) in which the relative motion amount (MV, MH) is smaller than a second threshold value (T_MV_P, 0), when it has been determined (expression (9)) by the focus necessity determination process (S15) that the cumulative motion amount (SUM_MV, SUM_MH) is larger than the first threshold value (T_MV), and causes the imaging section 200 to perform the focus operation when it has been determined that there have been the L frames in which the relative motion amount (MV, MH) is smaller than a second threshold value (T_MV_P, 0).

According to this configuration, the focus operation can be performed when it has been determined that the focus operation is required since the endoscope apparatus has moved to a large extent, and it has been determined that the motion due to the movement of the endoscope apparatus has decreased (i.e., the movement of the endoscope apparatus has stopped). This makes it possible to suppress a situation in which the focus state changes (e.g., wobbling occurs) before completion of the movement of the endoscope apparatus. It is also possible to suppress a situation in which the focus operation is performed while the endoscope apparatus is being moved, and the object is out of focus after completion of the movement of the endoscope apparatus. This makes it possible to provide a natural image (or an image with high visibility) to the user.

The number L of frames is a given number, and is used to determine whether or not the relative motion with respect to the imaging section 200 and the object is zero (or small). Specifically, the number L of frames is set so that it can be determined that the user does not move the imaging section 200 when the inter-frame motion is small (or almost zero). For example, the number L may be fixed, or may be set by the user.

According to the second embodiment, the motion amount calculation section 340 (processor) calculates a plurality of local motion amounts ($v_i$) (VE in FIGS. 8 and 10), calculates a correlation between each of the plurality of local motion amounts ($v_i$) and a peripheral local motion amount, and calculates the relative motion amount (MV, MH) based on a local motion amount among the plurality of local motion amounts that has the correlation higher than a given correlation (expressions (2) and (3)).

According to this configuration, since a local motion due to disturbance can be removed based on the correlation, the global motion (e.g., the motion over the entire image) can be extracted, and the cumulative motion amount can be calculated from the global motion. The term "disturbance" used herein refers to a motion that differs from that of tissue (i.e., background). Examples of the disturbance include a motion due to the manipulation of a treatment tool, noise, and the like. The term "global motion" used herein refers to the motion of tissue. More specifically, the term "global motion" used herein refers to a relative motion with respect to the tissue area that is observed using the endoscope apparatus, and the imaging section 200. For example, the entire tissue moves in an identical direction during a vertical-to-optical axis motion, and the tissue makes a motion toward the vanishing point, or makes a motion from the vanishing point, during a horizontal-to-optical axis motion. A motion due to disturbance (e.g., treatment tool) is a local motion that differs from these motions. According to the second embodiment, since the global motion can be extracted, it is possible to perform the focus operation using the motion of the imaging section 200 with respect to tissue as a trigger. Specifically, it is possible to exclude a motion within an image due to the manipulation of a treatment tool during an endoscopic procedure from a trigger.

According to the second embodiment, the relative motion amount includes one or more components. For example, the relative motion amount includes the vertical-to-optical axis motion amount MV and the horizontal-to-optical axis motion amount MH (two components). Note that the vertical-to-optical axis motion amount MV (two-dimensional vector) may be considered to be two components (i.e., the relative motion amount may include three components). In the third embodiment (described later) in which a 6-axis motion sensor outputs a 6-axis detection signal, the relative motion amount includes six components. When the six components are converted into the vertical-to-optical axis motion amount MV and the horizontal-to-optical axis motion amount MH, the relative motion amount includes two or three components.

The focus control section 350 (processor) calculates the cumulative motion amount with respect to each of the one or more components, performs the focus necessity determination process (S15) using a threshold value as the first threshold value, the threshold value corresponding to the cumulative motion amount calculated with respect to each of the one or more components, and causes the imaging section 200 to perform the focus operation when it has been determined that the cumulative motion amount calculated with respect to at least one of the one or more components is larger than the threshold value that corresponds to the cumulative motion amount. For example, the determination process is performed on the cumulative motion amount SUM_MV obtained by accumulating the vertical-to-optical axis motion amount MV using the threshold value T_MV (expression (9)), and the determination process is performed on the cumulative motion amount SUM_MH obtained by accumulating the horizontal-to-optical axis motion amount MH using the threshold value T_MH (expression (13)).

This makes it possible to calculate the cumulative motion amount with respect to each component of the motion, and determine whether or not the focus operation is required using the threshold value that corresponds to each component. The degree of movement that requires the focus operation (i.e., the degree of movement by which the object becomes out of focus) differs corresponding to the component of the motion. Therefore, it is possible to perform an accurate determination by providing a threshold value that corresponds to each component. Since the focus operation is performed when the cumulative motion amount that corresponds to at least one component is larger than the threshold value, it is possible to performs the focus operation when at least one component has a large moving amount.

According to the second embodiment, the motion amount calculation section 340 (processor) calculates the vertical-to-optical axis motion amount (MV) as the relative motion amount, the vertical-to-optical axis motion amount (MV) being a motion amount in the direction vertical to the optical axis of the imaging section 200. The focus control section 350 performs the focus necessity determination process using a vertical-to-optical axis motion threshold value (T_MV) as the first threshold value, the vertical-to-optical axis motion threshold value (T_MV) being a threshold value with respect to the cumulative motion amount (SUM_MV) obtained by accumulating the vertical-to-optical axis motion amount (MV) (expression (9)).

As illustrated in FIG. 5, the vertical-to-optical axis motion amount refers to a motion amount that is detected when the imaging area (imaging range) with respect to an object 6 (e.g., tissue) has been changed (moved) from an imaging area RA2 to an imaging area RA1. The area RA1 and the area RA2 differ from each other as to the center (i.e., the position at which the optical axis intersects the object 6). The area RA1 and the area RA2 may overlap with each other. Such a motion occurs due to the rotation (MA) (i.e., rotation around a direction that is not parallel to the optical axis) of the endoscope apparatus 2 (see FIG. 5), or the parallel movement (i.e., parallel movement in a direction that is not parallel to the optical axis) of the endoscope apparatus 2.

It is possible to detect a change (movement) in the imaging range (area of interest) with respect to the object by utilizing the vertical-to-optical axis motion amount MV, and perform the focus operation when the imaging range has changed (changed to a large extent). For example, it is possible to bring the object into focus, and provide a clear image to the user when the imaging range has been moved by one screen, and a completely different object has been observed, or when the imaging range has been moved (shifted) by half of the screen.

According to the second embodiment, the motion amount calculation section 340 (processor) calculates a plurality of local motion amounts ($v_i$) based on the captured image that has been captured by the imaging section 200, calculates the average value of the plurality of local motion amounts ($v_i$) on a frame basis, and calculates the average value to be the vertical-to-optical axis motion amount (MV) (expression (1)).

According to this configuration, it is possible to calculate the global motion amount of the object from the local motion amounts at a plurality of positions within the image. Since tissue accounts for a large area as compared with a treatment tool when an endoscopic procedure is performed, it is possible to calculate the global motion amount of the tissue by averaging the local motion amounts. Moreover, random motions due to disturbance are averaged within the image by the intra-frame averaging process, and are accumulated over a plurality of frames so that the random motions due to disturbance are temporally averaged. This makes it possible to extract the global motion of the tissue.

According to the second embodiment, the motion amount calculation section 340 (processor) calculates a plurality of local motion amounts ($v_i$), generates a histogram with respect to magnitude and direction from the plurality of local motion amounts ($v_i$) on a frame basis (FIG. 9), and calculates a bin of the histogram that has the maximum value to be the vertical-to-optical axis motion amount (MV).

According to this configuration, it is possible to select the global motion amount of the object from the local motion amounts at a plurality of positions within the image, and extract the selected global motion amount to be the vertical-to-optical axis motion amount MV Specifically, since tissue accounts for a large area as compared with a treatment tool when an endoscopic procedure is performed, it is considered that the global motion amount of the tissue corresponds to the bin of the histogram that has the maximum value. Therefore, it is possible to extract the global motion amount excluding the motion amount due to disturbance (e.g., treatment tool) by selecting the bin of the histogram that has the maximum value.

According to the second embodiment, the motion amount calculation section 340 (processor) calculates the vertical-to-optical axis motion amount (MV) as the relative motion amount, the vertical-to-optical axis motion amount (MV) being a motion amount in the direction vertical to the optical axis of the imaging section 200. The focus control section 350 performs the focus feasibility determination process (S17) on the vertical-to-optical axis motion amount (MV).

According to this configuration, it is possible to trigger the focus operation when it is determined that the imaging range is stationary (i.e., the user does not move the imaging range). For example, when the user has moved the imaging section 200 in order to change the observation target (e.g., the observation target internal organ, or the observation target area), it is determined that the focus operation is required when the imaging section 200 has been moved by a distance equal to or longer than a given distance. The focus operation is not triggered during a period in which the imaging section 200 is being moved, and a trigger signal is transmitted to the imaging section 200 when it has been determined that the imaging section 200 has become stationary.

According to the second embodiment, the motion amount calculation section 340 (processor) calculates the horizontal-to-optical axis motion amount (MH) as the relative motion amount, the horizontal-to-optical axis motion amount (MH) being a motion amount in the direction horizontal (parallel) to the optical axis of the imaging section 200. The focus control section 350 performs the focus necessity determination process (S15) using a horizontal-to-optical axis motion threshold value (T_MH) as the first threshold value, the horizontal-to-optical axis motion threshold value (T_MH) being a threshold value with respect to the cumulative motion amount (SUM_MH) obtained by accumulating the horizontal-to-optical axis motion amount (MH) (expression (13)).

Figure 6:
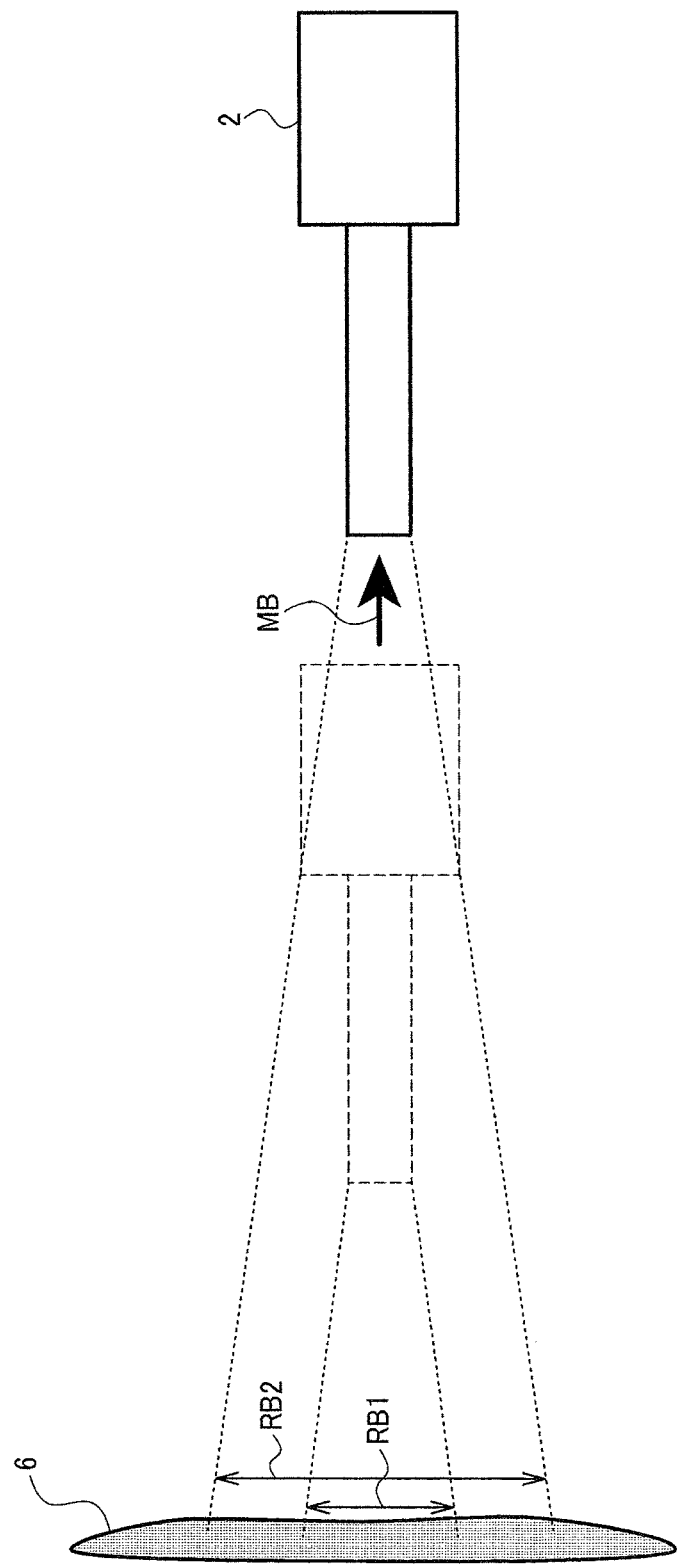
FIG. 6 is a view illustrating a horizontal-to-optical axis motion.

As illustrated in FIG. 6, the horizontal-to-optical axis motion amount refers to a motion amount that is detected when the imaging area (imaging range) with respect to an object 6 (e.g., tissue) has been enlarged or reduced from an imaging area RB1 to an imaging area RB2. The area 1 and the area RB2 are identical to each other as to the center (i.e., the position at which the optical axis intersects the object 6).

It is considered that a horizontal-to-optical axis motion and a vertical-to-optical axis motion normally occur in combination. In such a case, the area RB1 and the area RB2 need not be identical to each other as to the center. Specifically, the imaging area is enlarged or reduced when a horizontal-to-optical axis motion has occurred irrespective of whether or not the area RB1 and the area RB2 are identical to each other as to the center. Such a horizontal-to-optical axis motion occurs when the endoscope apparatus 2 has been moved (MB) in the direction horizontal (parallel) to the optical axis (see FIG. 6).

It is possible to estimate whether or not the object lies outside the depth of field by utilizing the horizontal-to-optical axis motion amount MH, and perform the focus operation when it is estimated that the object lies outside the depth of field (when the object has moved to a large extent from the in-focus object plane position). This makes it possible to bring the object into focus that has become out of focus (or is about to become out of focus), and provide a clear image to the user.

According to the second embodiment, the motion amount calculation section 340 (processor) calculates a plurality of local motion vectors ($v_i$) (VE in FIG. 10), calculates the vanishing point (VP) of the plurality of local motion vectors ($v_i$) on a frame basis, calculates an evaluation value (i.e., the sum of the distances) of the vanishing point (VP) based on the distance between a straight line obtained by extending each of the plurality of local motion vectors ($v_i$) and the vanishing point (VP), and calculates the horizontal-to-optical axis motion amount (MH) with respect to a frame in which the evaluation value is larger than a given value.

According to this configuration, it is possible to determine whether or not a horizontal-to-optical axis motion has occurred from the evaluation value of the vanishing point VP, and calculate the horizontal-to-optical axis motion amount MH with respect to a frame for which it has been determined that a horizontal-to-optical axis motion has occurred. Specifically, when the vanishing point VP is unclear (i.e., when the reliability of the vanishing point VP is low), it is determined that a horizontal-to-optical axis motion has not occurred (or the occurrence of a horizontal-to-optical axis motion cannot be determined due to disturbance or the like). Therefore, the cumulative motion amount can be calculated from a frame in which a horizontal-to-optical axis motion has occurred, by excluding a frame in which the evaluation value of the vanishing point VP is low.

According to the second embodiment, the motion amount calculation section 340 (processor) calculates the horizontal-to-optical axis motion amount (MH) (expression (4)) that differs in sign corresponding to whether the imaging section 200 moves closer to the object, or moves away from the object.

The object lies outside the depth of field when the imaging section 200 has continuously moved closer to the object, or continuously moved away from the object. The cumulative motion amount increases when the imaging section 200 has continuously moved closer to the object, or continuously moved away from the object, and it is possible to trigger the focus operation, by utilizing the horizontal-to-optical axis motion amount MH that differs in sign corresponding to whether the imaging section 200 moves closer to the object, or moves away from the object. Specifically, since the cumulative motion amount does not increase due to accumulation when the imaging section 200 randomly moves closer to the object, or moves away from the object, the focus operation is not triggered, and an unnecessary change in focus does not occur.

Figure 12:
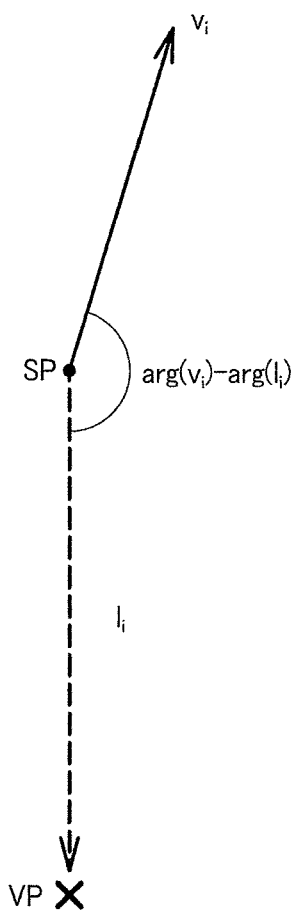
FIG. 12 is a view illustrating a process that determines the direction of a horizontal-to-optical axis motion.

According to the second embodiment, the motion amount calculation section 340 (processor) calculates a plurality of local motion vectors ($v_i$), calculates the vanishing point (VP) of the plurality of local motion vectors ($v_i$) on a frame basis, calculates information that changes corresponding to the angle ($\arg(v)-\arg(l_i)$) formed by a vector ($l_i$) and each of the plurality of local motion vectors ($v_i$), the vector ($l_i$) connecting the start point (SP) of each of the plurality of local motion vectors (v) and the vanishing point (VP) (FIG. 12), and determines whether the imaging section 200 moves closer to the object, or moves away from the object, based on the information (expressions (5) to (7)).

The information that changes corresponding to the angle formed by the motion vector $v_i$ and the vector $l_i$ may be the angle ($\arg(v_i)-\arg(l_i)$) (expression (5)), or may be a value that is a function of the angle (e.g., a value obtained by normalizing the inner product of the motion vector $v_i$ and the vector $l_i$ (expressions (6) and (7))).

It is possible to determine the direction (i.e., a motion that moves closer to the object, or a motion that moves away from the object) of the horizontal-to-optical axis motion by utilizing the information that changes corresponding to the angle formed by the motion vector $v_i$ and the vector $l_i$. Specifically, when the horizontal-to-optical axis motion is a motion that moves closer to the object, the local motion vectors have a direction toward the vanishing point VP, and the motion vector $v_i$ and the vector $l_i$ are almost identical to each other as to the direction (i.e., the angle formed by the motion vector $v_i$ and the vector $l_i$ is close to "0"). On the other hand, when the horizontal-to-optical axis motion is a motion that moves away from the object, the local motion vectors have a direction away from the vanishing point VP, and the motion vector $v_i$ and the vector $l_i$ are almost opposite to each other as to the direction (i.e., the angle formed by the motion vector $v_i$ and the vector $l_i$ is close to "+π" or "−π"). Therefore, the direction of the horizontal-to-optical axis motion can be determined based on the angle formed by the motion vector $v_i$ and the vector $l_i$.

According to the second embodiment, the motion amount calculation section 340 (processor) calculates the horizontal-to-optical axis motion amount (MH) as the relative motion amount, the horizontal-to-optical axis motion amount (MH) being a motion amount in the direction horizontal (parallel) to the optical axis of the imaging section 200. The focus control section 350 performs the focus feasibility determination process (S17) on the horizontal-to-optical axis motion amount (MH).

According to this configuration, it is possible to trigger the focus operation when it is determined that no motion has occurred in the optical axis direction (i.e., the user does not move the imaging section 200 in the optical axis direction). For example, when the user has moved the imaging section 200 in order to change the observation target (e.g., observe an internal organ that is situated in front of, or on the rear side of, the current observation target internal organ), or change (increase or decrease) the observation range, it is determined that the focus operation is required when the imaging section 200 has been moved by a distance equal to or longer than a given distance. The focus operation is not triggered during a period in which the imaging section 200 is being moved, and a trigger signal is transmitted to the imaging section 200 when it has been determined that the imaging section 200 has become stationary.

According to the second embodiment, the focus control section 350 (processor) sets the first threshold value (TA2) when the in-focus object plane position of the imaging section 200 is set to a second position (PA2) to be smaller than the first threshold value (TA1) when the in-focus object plane position is set to a first position (PA1 in FIG. 15) (TA1>TA2), the second position (PA2) being nearer than the first position (PA1).

For example, a table in which the in-focus object plane position (e.g., position information about the focus lens 210) is linked to the first threshold value may be stored in a storage section (not illustrated in the drawings), and the first threshold value may be set by referring to the table. Alternatively, the first threshold value that corresponds to a given in-focus object plane position (reference in-focus object plane position) may be used as a reference value, and the first threshold value may be set by correcting the reference value corresponding to the actual in-focus object plane position.

It is possible to deal with a change in the depth of field due to a change in the in-focus object plane position by thus changing the threshold value corresponding to the in-focus object plane position (i.e., corresponding to whether the near side or the infinity side is in focus). When a normal optical system is used, the depth of field becomes shallow when the near side is in focus, and it is likely that the object lies outside the depth of field. However, the in-focus state can be maintained by decreasing the threshold value on the near side. On the other hand, the depth of field becomes deep when the infinity side is in focus, and it is unlikely that the object lies outside the depth of field. Therefore, an unnecessary focus operation can be suppressed by increasing the threshold value on the infinity side.

According to the second embodiment, the motion amount calculation section 340 (processor) calculates the vertical-to-optical axis motion amount (MV) as the relative motion amount, the vertical-to-optical axis motion amount (MV) being a motion amount in the direction vertical to the optical axis of the imaging section 200. The focus control section 350 performs the focus necessity determination process (S15) using a first-direction threshold value (T_MV_V) and a second-direction threshold value (T_MV_H) as the first threshold value, the first-direction threshold value (T_MV_V) being a threshold value with respect to a first-direction (vertical scan direction or y-direction) component (SUM_MV_V) of the cumulative motion amount (SUM_MV), and the second-direction threshold value (T_MV_H) being a threshold value with respect to a second-direction (horizontal scan direction or x-direction) component (SUM_MV_H) of the cumulative motion amount (SUM_MV), and sets the first-direction threshold value (T_MV_V) and the second-direction threshold value (T_MV_H) to values that differ from each other (expressions (10) and (11)).

According to this configuration, it is possible to change the threshold value, and cause the moving amount that triggers the focus operation, between a case where a movement has occurred in the upward-downward direction with respect to the image, and a case where a movement has occurred in the rightward-leftward direction with respect to the image. For example, when the vertical size and the horizontal size of the image differ from each other, the threshold value may be changed corresponding to the size of the image. Alternatively, when a change in the depth of the internal organ differs between the upward-downward direction and the rightward-leftward direction due to the structure of a human body, gravity, and the like, the threshold value may be changed corresponding to the change in the depth of the internal organ.

According to the second embodiment, the motion amount calculation section 340 (processor) calculates the horizontal-to-optical axis motion amount (MH) as the relative motion amount, the horizontal-to-optical axis motion amount (MH) being a motion amount in the direction horizontal (parallel) to the optical axis of the imaging section 200. The focus control section 350 performs the focus necessity determination process using a close-movement threshold value (T_MH_N) and an away-movement threshold value (T_MH_F) as the first threshold value, the close-movement threshold value (T_MH_N) being a threshold value when the cumulative motion amount (SUM_MH) corresponds to a case where the imaging section 200 moves closer to the object, and the away-movement threshold value (T_MH_F) being a threshold value when the cumulative motion amount (SUM_MH) corresponds to a case where the imaging section 200 moves away from the object, and sets the absolute value of the close-movement threshold value (T_MH_N) to be smaller than the absolute value of the away-movement threshold value (T_MH_F) (expressions (15) and (16)).

It is possible to deal with the difference in depth of field between the near side and the infinity side by thus changing the threshold value corresponding to the direction (i.e., a motion that moves closer to the object, or a motion that moves away from the object) of the horizontal-to-optical axis motion. Specifically, when a normal optical system is used, the depth of field on the near side is shallower than the depth of field on the infinity side when the in-focus object plane position is constant. Therefore, it is likely that the object lies outside the depth of field when the imaging section 200 moves closer to the object as compared with the case where the imaging section 200 moves away from the object. According to the second embodiment, it is possible to easily maintain the in-focus state when the imaging section 200 moves closer to the object in the direction in which the depth of field becomes shallow, and suppress an unnecessary focus operation when the imaging section 200 moves away from the object in the direction in which the depth of field becomes deep, by setting the close-movement threshold value to be smaller than the away-movement threshold value.

According to the second embodiment, the motion amount calculation section 340 (processor) calculates the cumulative motion amount (SUM_MV, SUM_MH) over the N frames that start from a reference frame (e.g., first frame) after the focus operation has been set to a standby state, to the current frame.

According to this configuration, since the motion amount after the object has been brought into focus (after the focus operation has been completed) is accumulated, it is possible to determine the total moving amount after the object has been brought into focus. Specifically, it is possible to trigger the focus operation after determining whether or not the movement from the object that has been brought into focus has reached the moving amount that requires the focus operation. Moreover, even when the motion is small (slow), it is possible to trigger the focus operation when the total moving amount has increased, by accumulating the motion amount after the focus operation has been set to the standby state.

Note that the motion amount calculation section 340 (processor) may calculate the cumulative motion amount (SUM_MV, SUM_MH) over the N frames that start from a reference frame (e.g., first frame) after the accumulation frame count (N) with respect to the relative motion amount (MV, MH) has been reset, to the current frame.

When the motion amount is continuously accumulated after the focus operation has been set to the standby state, an error between the cumulative motion amount and the actual moving amount increases since an error (e.g., noise and offset) is also accumulated. Therefore, it is possible to suppress an increase in error by resetting the cumulative motion amount, and accumulating the motion amount again.

3. Third Embodiment

Figure 17:
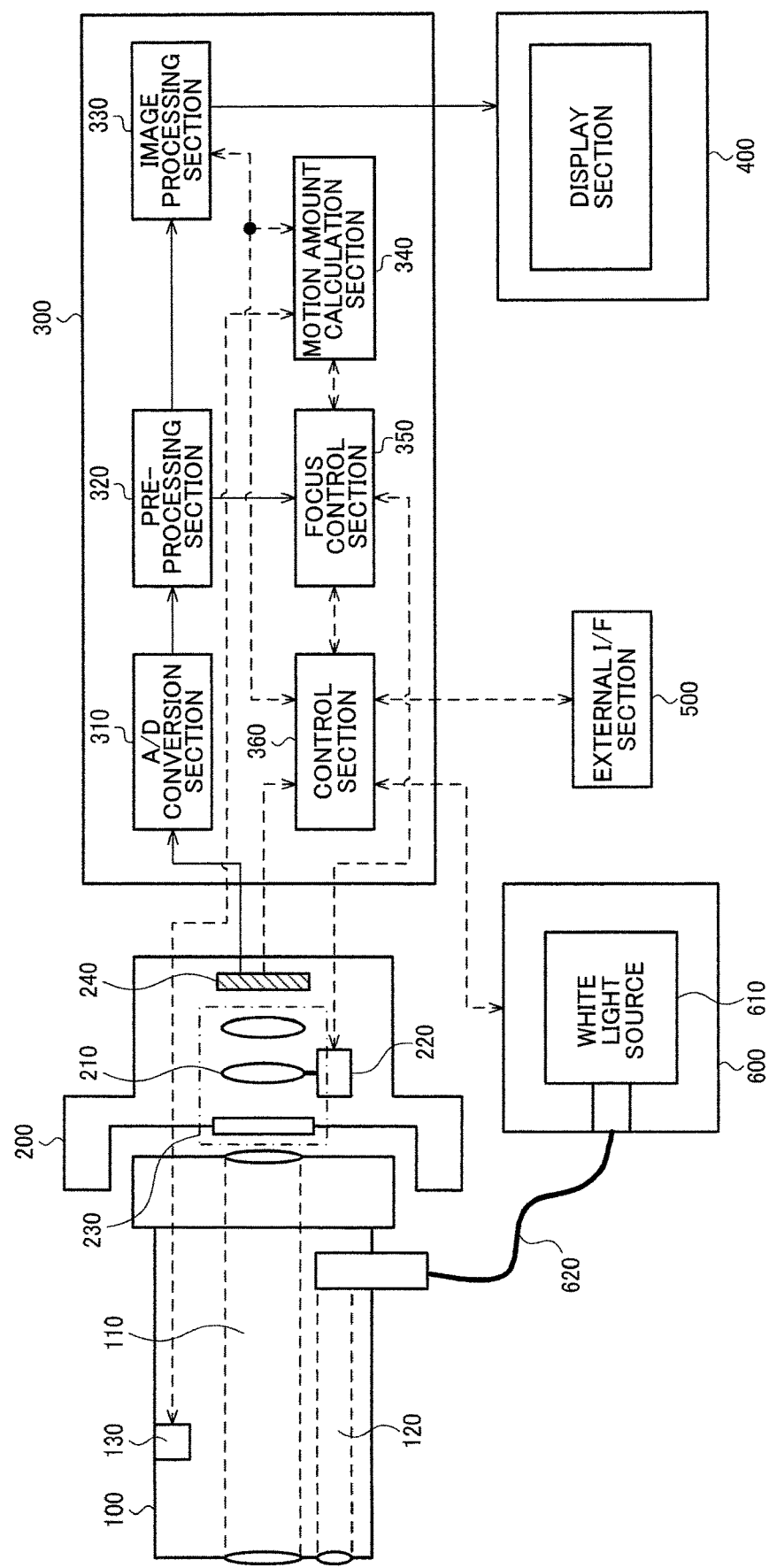
FIG. 17 illustrates a configuration example of an endoscope apparatus (third embodiment).

FIG. 17 illustrates a configuration example of an endoscope apparatus according to a third embodiment. The endoscope apparatus includes a rigid scope 100 that is inserted into a body, an imaging section 200 that is connected to the rigid scope 100, a processing section 300, a display section 400, an external I/F section 500, and a light source section 600. The endoscope apparatus is configured in the same manner as described above in connection with the second embodiment, except for the rigid scope 100 and the processing section 300, and description of the elements other than the rigid scope 100 and the processing section 300 is omitted.

The rigid scope 100 includes a 6-axis motion sensor 130 that detects triaxial rotational motions and triaxial translational motions. The rigid scope 100 outputs a detection signal (motion signal) from the motion sensor 130 to the processing section 300. For example, the motion sensor 130 includes an angular acceleration sensor (gyro sensor) that detects angular accelerations around three axes (i.e., an x-axis, a y-axis, and a z-axis that are orthogonal to each other), and an acceleration sensor that detects accelerations in triaxial (i.e., x-axis, y-axis, and z-axis) directions. The motion sensor 130 operates at a frequency sufficiently higher than the operating frequency (frame frequency) of the image sensor 240. The motion sensor 130 integrates the detected angular accelerations and accelerations using an integrator (not illustrated in the drawings), and outputs the integration results as a change in angle and a change in position. The integration start/end timing is synchronized with the operation timing (image capture timing) of the image sensor 240. The motion signal represents a change in angle and a change in position of the rigid scope 100 that have occurred between the operation timings (frames) of the image sensor 240.

The processing section 300 includes an A/D conversion section 310, a pre-processing section 320, an image processing section 330, a motion amount calculation section 340, a focus control section 350, and a control section 360. The processing section 300 is configured in the same manner as described above in connection with the second embodiment, except for the motion amount calculation section 340, and description of the elements other than the motion amount calculation section 340 is omitted.

The motion amount calculation section 340 calculates the motion amount based on the detection signal output from the motion sensor 130, and the in-focus object plane position. The motion amount calculation section 340 outputs the calculated motion amount to the focus control section 350. The motion amount includes a vertical-to-optical axis motion amount and a horizontal-to-optical axis motion amount in the same manner as in the second embodiment. The horizontal-to-optical axis component of a change in position (motion in the real space) is used as the horizontal-to-optical axis motion amount. Therefore, the horizontal-to-optical axis motion amount according to the third embodiment has a sign and a magnitude (e.g., −3 mm or +10 mm). The focus control section 350 uses the horizontal-to-optical axis motion amount as the horizontal-to-optical axis motion amount MH, accumulates the horizontal-to-optical axis motion amount, and performs the determination process (focus necessity determination process and focus feasibility determination process) in the same manner as described above in connection with the second embodiment. The vertical-to-optical axis motion amount within the image is calculated from the vertical-to-optical axis component (i.e., the yaw component and the pitch component of a change in angle) of a change in position (motion in the real space). More specifically, the vertical-to-optical axis motion amount is the sum of a term that converts a change in position in the real space into the motion amount within the image based on the imaging magnification, and a term that converts a change in angle in the real space into the motion amount within the image based on the ratio with respect to the maximum angle of view (see the following expressions (18) and (19)).

$$MV\_UD = HEAVE \times ZOOM(P) + PITCH \div MAX\_ANGLE\_UD \times MAX\_PIXEL\_UD \quad (18)$$

$$MV\_LR = SWAY \times ZOOM(P) + YAW \div MAX\_ANGLE\_LR \times MAX\_PIXCEL\_LR \quad (19)$$

Note that HEAVE is a component of the change in position in the upward-downward direction, and SWAY is a component of the change in position in the rightward-leftward direction. ZOOM(P) is the imaging magnification at the object in-focus position P. PITCH is the pitch component of the change in angle, and YAW is the yaw component of the change in angle. MAX_ANGLE_UD is the maximum angle of view of the rigid scope 100 in the upward-downward direction, and MAX_ANGLE_LR is the maximum angle of view of the rigid scope 100 in the rightward-leftward direction. MAX_PIXEL_UD is the maximum number of pixels of the image sensor 240 in the upward-downward direction, and MAX_PIXEL_LR is the maximum number of pixels of the image sensor 240 in the rightward-leftward direction.

The focus control section 350 uses the two-dimensional vector that includes a component MV_UD in the upward-downward direction and a component MV_LR in the rightward-leftward direction as the vertical-to-optical axis motion amount MV, and performs the determination process (focus necessity determination process and focus feasibility determination process) in the same manner as described above in connection with the second embodiment.

Although an example in which the rigid scope 100 includes the motion sensor 130, and the motion amount calculation section 340 calculates the motion amount based on the motion signal output from the motion sensor 130, has been described above, the rigid scope 100 may include a position sensor (e.g., magnetic position sensor), and the motion amount calculation section 340 may calculate the motion amount based on a temporal change in position information output from the position sensor.

According to the third embodiment, reflected light from the object is captured as an image using the imaging section 200 that can perform the focus operation, and includes the motion sensor 130 that detects an angular acceleration and an acceleration. The relative motion amount (MV, MH) with respect to the imaging section 200 and the object is calculated from the output from the motion sensor 130. When the net motion amount obtained by accumulating the motion amount (MV, MH) over a plurality of frames has exceeded a given threshold value, it is determined that the focus operation is required, and the imaging section 200 performs the focus operation. Since the focus operation is performed when the motion amount obtained by accumulating the motion amount over a plurality of frames has exceeded a given amount, it is possible to implement an AF control process that performs the focus operation when the object has become out of focus even when the motion is slow, and does not perform the focus operation when an unintentional momentary motion has occurred.

The embodiments to which the invention is applied and the modifications thereof have been described above. Note that the invention is not limited to the above embodiments and the modifications thereof. Various modifications and variations may be made without departing from the scope of the invention. A plurality of elements described above in connection with the embodiments and the modifications thereof may be appropriately combined to implement various configurations. For example, some of the elements described above in connection with the embodiments and the modifications thereof may be omitted. Some of the elements described above in connection with different embodiments or modifications thereof may be appropriately combined. Specifically, various modifications and applications are possible without materially departing from the novel teachings and advantages of the invention. Any term cited with a different term having a broader meaning or the same meaning at least once in the specification and the drawings can be replaced by the different term in any place in the specification and the drawings.

The invention claimed is:

1. An endoscope apparatus comprising:
   a processor comprising hardware, the processor being configured to implement:
      a motion amount calculation process that calculates a relative motion amount that is a relative motion amount with respect to an imaging section and an object; and
      a focus control process that is performed on the imaging section,
   wherein:
   the relative motion amount comprises information about a magnitude of a motion and information about a direction of a motion,
   the motion amount calculation process comprises calculating a plurality of local motion amounts, calculating a correlation between each of the plurality of local motion amounts and a peripheral local motion amount, and calculating the relative motion amount based on a local motion amount among the plurality of local motion amounts whose calculated correlation is higher than a given correlation,
   the focus control process comprises, in a standby state under which a focus operation is not being performed, (i) calculating a cumulative motion amount by accumulating the relative motion amount over N frames (wherein N is a natural number equal to or larger than 3), and (ii) performing a focus necessity determination process that determines whether or not the cumulative motion amount is larger than a first threshold value, and then causing the imaging section to perform the focus operation when it has been determined in the focus necessity determination process that the cumulative motion amount is larger than the first threshold value, and
   the focus operation is switched to the standby state when it has been determined that the object has been brought into focus by performing the focus operation.

2. The endoscope apparatus as defined in claim 1, wherein the focus control process comprises performing a focus feasibility determination process that determines whether or not there have been L frames (wherein L is a natural number equal to or larger than 3) in which the relative motion amount is smaller than a second threshold value, when it has been determined in the focus necessity determination process that the cumulative motion amount is larger than the first threshold value, and causing the imaging section to perform the focus operation when it has been determined that there have been the L frames in which the relative motion amount is smaller than the second threshold value.

3. The endoscope apparatus as defined in claim 2, wherein:
   the motion amount calculation process calculates a vertical-to-optical axis motion amount as the relative motion amount, the vertical-to-optical axis motion amount being a motion amount in a direction vertical to an optical axis of the imaging section, and
   the focus control process performs the focus feasibility determination process based on the vertical-to-optical axis motion amount.

4. The endoscope apparatus as defined in claim 2, wherein:
   the motion amount calculation process calculates a horizontal-to-optical axis motion amount as the relative motion amount, the horizontal-to-optical axis motion amount being a motion amount in a direction horizontal to an optical axis of the imaging section, and
   the focus control process performs the focus feasibility determination process based on the horizontal-to-optical axis motion amount.

5. The endoscope apparatus as defined in claim 2, wherein:
   the motion amount calculation process calculates a vertical-to-optical axis motion amount and a horizontal-to-optical axis motion amount as the relative motion amount, the vertical-to-optical axis motion amount being a motion amount in a direction vertical to an optical axis of the imaging section, and the horizontal-to-optical axis motion amount being a motion amount in a direction horizontal to the optical axis of the imaging section, and
   the focus control process causes the imaging section to perform the focus operation when it has been determined that there have been the L frames in which the cumulative motion amount obtained by accumulating the vertical-to-optical axis motion amount and the cumulative motion amount obtained by accumulating the horizontal-to-optical axis motion amount are smaller than the second threshold value.

6. The endoscope apparatus as defined in claim 1, wherein:
   the relative motion amount comprises one or more components, and
   the focus control process comprises calculating the cumulative motion amount with respect to each of the one or more components, performing the focus necessity determination process using a threshold value as the first threshold value, the threshold value corresponding to the cumulative motion amount calculated with respect to each of the one or more components, and causing the imaging section to perform the focus operation when it has been determined that the cumulative motion amount calculated with respect to at least one of the one or more components is larger than the threshold value that corresponds to the cumulative motion amount.

7. The endoscope apparatus as defined in claim 1, wherein:
   the motion amount calculation process calculates a vertical-to-optical axis motion amount as the relative motion amount, the vertical-to-optical axis motion amount being a motion amount in a direction vertical to an optical axis of the imaging section, and the focus control process performs the focus necessity determination process using a vertical-to-optical axis motion threshold value as the first threshold value, the vertical-to-optical axis motion threshold value being a threshold value with respect to the cumulative motion amount obtained by accumulating the vertical-to-optical axis motion amount.

8. The endoscope apparatus as defined in claim 7, wherein the motion amount calculation process comprises calculating a plurality of local motion amounts based on a captured image that has been captured by the imaging section, calculating an average value of the plurality of local motion amounts on a frame basis, and taking the calculated average value to be the vertical-to-optical axis motion amount.

9. The endoscope apparatus as defined in claim 7, wherein the motion amount calculation process comprises calculating a plurality of local motion amounts, generating a histogram with respect to magnitude and direction from the plurality of local motion amounts on a frame basis, and taking a bin of the histogram that has a maximum value to be the vertical-to-optical axis motion amount.

10. The endoscope apparatus as defined in claim 1, wherein:
the motion amount calculation process calculates a horizontal-to-optical axis motion amount as the relative motion amount, the horizontal-to-optical axis motion amount being a motion amount in a direction horizontal to an optical axis of the imaging section, and
the focus control process performs the focus necessity determination process using a horizontal-to-optical axis motion threshold value as the first threshold value, the horizontal-to-optical axis motion threshold value being a threshold value with respect to the cumulative motion amount obtained by accumulating the horizontal-to-optical axis motion amount.

11. The endoscope apparatus as defined in claim 10, wherein the motion amount calculation process comprises calculating a plurality of local motion vectors, calculating a vanishing point of the plurality of local motion vectors on a frame basis, calculating an evaluation value of the vanishing point based on a distance between a straight line obtained by extending each of the plurality of local motion vectors and the vanishing point, and calculating the horizontal-to-optical axis motion amount with respect to a frame in which the evaluation value is larger than a given value.

12. The endoscope apparatus as defined in claim 10, wherein calculated horizontal-to-optical axis motion amount differs in sign based on whether the imaging section moves closer to the object or moves away from the object.

13. The endoscope apparatus as defined in claim 12, wherein the motion amount calculation process comprises calculating a plurality of local motion vectors, calculating a vanishing point of the plurality of local motion vectors on a frame basis, calculating information that changes corresponding to an angle formed by a vector and each of the plurality of local motion vectors, the vector connecting a start point of each of the plurality of local motion vectors and the vanishing point, and determining whether the imaging section moves closer to the object or moves away from the object based on the information.

14. The endoscope apparatus as defined in claim 1, wherein:
the motion amount calculation process calculates a vertical-to-optical axis motion amount and a horizontal-to-optical axis motion amount as the relative motion amount, the vertical-to-optical axis motion amount being a motion amount in a direction vertical to an optical axis of the imaging section, and the horizontal-to-optical axis motion amount being a motion amount in a direction horizontal to the optical axis of the imaging section, and the focus control process performs the focus necessity determination process using a vertical-to-optical axis motion threshold value as the first threshold value, the vertical-to-optical axis motion threshold value being a threshold value with respect to the cumulative motion amount obtained by accumulating the vertical-to-optical axis motion amount, performs the focus necessity determination process using a horizontal-to-optical axis motion threshold value as the first threshold value, the horizontal-to-optical axis motion threshold value being a threshold value with respect to the cumulative motion amount obtained by accumulating the horizontal-to-optical axis motion amount, and causes the imaging section to perform the focus operation when it has been determined that the cumulative motion amount obtained by accumulating the vertical-to-optical axis motion amount is larger than the vertical-to-optical axis motion threshold value, or it has been determined that the cumulative motion amount obtained by accumulating the horizontal-to-optical axis motion amount is larger than the horizontal-to-optical axis motion threshold value.

15. The endoscope apparatus as defined in claim 1, wherein the focus control process comprises setting the first threshold value such that, when an in-focus object plane position of the imaging section is set to a second position, the first threshold is set to be smaller than the first threshold value when the in-focus object plane position is set to a first position, the second position being nearer than the first position.

16. The endoscope apparatus as defined in claim 1, wherein:
the motion amount calculation process calculates a vertical-to-optical axis motion amount as the relative motion amount, the vertical-to-optical axis motion amount being a motion amount in a direction vertical to an optical axis of the imaging section, and
the focus control process performs the focus necessity determination process using a first-direction threshold value and a second-direction threshold value as the first threshold value, the first-direction threshold value being a threshold value with respect to a first-direction component of the cumulative motion amount, and the second-direction threshold value being a threshold value with respect to a second-direction component of the cumulative motion amount, the first-direction threshold value and the second-direction threshold value being set to values that differ from each other.

17. The endoscope apparatus as defined in claim 1, wherein:
the motion amount calculation process calculates a horizontal-to-optical axis motion amount as the relative motion amount, the horizontal-to-optical axis motion amount being a motion amount in a direction horizontal to an optical axis of the imaging section, and
the focus control process performs the focus necessity determination process using a close-movement threshold value and an away-movement threshold value as the first threshold value, the close-movement threshold value being a threshold value when the cumulative motion amount corresponds to a case where the imaging section moves closer to the object, and the away-movement threshold value being a threshold value when the cumulative motion amount corresponds to a case where the imaging section moves away from the object, an absolute value of the close-movement threshold value being set to be smaller than an absolute value of the away-movement threshold value.

18. The endoscope apparatus as defined in claim 1, wherein the motion amount calculation process calculates the cumulative motion amount over the N frames that start from a reference frame after the focus operation has been set to the standby state, to a current frame.

19. The endoscope apparatus as defined in claim 1, wherein the motion amount calculation process calculates the cumulative motion amount over the N frames that start from a reference frame after an accumulation frame count with respect to the relative motion amount has been reset, to a current frame.

20. The endoscope apparatus as defined in claim 1, wherein the motion amount calculation process calculates a motion vector as the relative motion amount based on a captured image that has been captured by the imaging section.

21. The endoscope apparatus as defined in claim 1, wherein:
   the imaging section comprises at least one of a motion sensor and a position sensor, and
   the motion amount calculation process calculates the relative motion amount based on a signal from at least one of the motion sensor and the position sensor.

* * * * *